(12) United States Patent
Burgdorf et al.

(10) Patent No.: US 8,236,824 B2
(45) Date of Patent: Aug. 7, 2012

(54) N-(PYRAZOLE-3-YL)-BENZAMIDE DERIVATIVES AS GLUCOKINASE ACTIVATORS

(75) Inventors: Lars Thore Burgdorf, Frankfurt am Main (DE); Norbert Beier, Reinheim (DE); Johannes Gleitz, Darmstadt (DE); Ulrich Emde, Darmstadt (DE); Christine Charon, Gometz-le-Chatel (FR); Denis Carniato, Marcoussis (FR)

(73) Assignee: Merck Patent Gesellschaft mit Beschränkter Haftung, Darmstadt (DE)

( * ) Notice: Subject to any disclaimer, the term of this patent is extended or adjusted under 35 U.S.C. 154(b) by 214 days.

(21) Appl. No.: 12/682,049

(22) PCT Filed: Sep. 9, 2008

(86) PCT No.: PCT/EP2008/007365
§ 371 (c)(1),
(2), (4) Date: Apr. 8, 2010

(87) PCT Pub. No.: WO2009/046802
PCT Pub. Date: Apr. 16, 2009

(65) Prior Publication Data
US 2010/0210690 A1  Aug. 19, 2010

(30) Foreign Application Priority Data
Oct. 9, 2007  (EP) ..................... 07019692

(51) Int. Cl.
| | |
|---|---|
| *A61K 31/4439* | (2006.01) |
| *A61K 31/415* | (2006.01) |
| *C07D 401/06* | (2006.01) |
| *C07D 231/40* | (2006.01) |
| *A61P 3/04* | (2006.01) |
| *A61P 13/12* | (2006.01) |

(52) U.S. Cl. ............ 514/341; 514/407; 546/275.4; 548/365.7; 548/372.5

(58) Field of Classification Search .......... None
See application file for complete search history.

(56) References Cited

U.S. PATENT DOCUMENTS
2006/0167053 A1  7/2006  Ilno et al.
2008/0015203 A1  1/2008  Johnstone et al.

FOREIGN PATENT DOCUMENTS
| EP | 1 600 442 A1 | 11/2005 |
|---|---|---|
| WO | WO 03/015774 A1 | 2/2003 |
| WO | WO 2005/121110 A1 | 12/2005 |
| WO | WO 2006/114313 A1 | 11/2006 |
| WO | WO 2007/113289 A1 | 10/2007 |
| WO | WO 2008/118758 A1 | 10/2008 |

OTHER PUBLICATIONS

International Search Report of PCT/EP2008/007365 (Jan. 13, 2009).

*Primary Examiner* — Kamal Saeed
(74) *Attorney, Agent, or Firm* — Millen, White, Zelano & Branigan, P.C.

(57) ABSTRACT

Novel heterocyclic compounds of the formula I

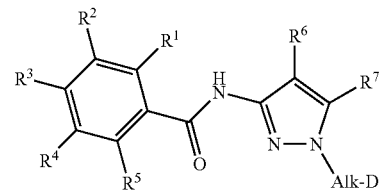

in which $R^1$, $R^2$, $R^3$, $R^4$, $R^5$, $R^6$, $R^7$, Alk and D have the meanings indicated in claim 1,
are activators of glucokinase and can be used for the prevention and/or treatment of Diabetes Typ 1 and 2, obesity, neuropathy and/or nephropathy.

22 Claims, No Drawings

N-(PYRAZOLE-3-YL)-BENZAMIDE DERIVATIVES AS GLUCOKINASE ACTIVATORS

BACKGROUND OF THE INVENTION

The invention had the object of finding novel compounds having valuable properties, in particular those which can be used for the preparation of medicaments.

The present invention relates to compounds that are useful in the treatment and/or prevention of diseases mediated by deficient levels of glucokinase activity, such as diabetes mellitus, and methods of preparing such compounds. Also provided are methods of treating diseases and disorders characterized by underactivation of glucokinase activity or which can be treated by activating glucokinase, comprising administering an effective amount of a compound of this invention.

The identification of small compounds which specifically activate, regulate and/or modulate signal transduction of glucokinase is therefore desirable and an aim of the present invention. Moreover, aim of this invention was the preparation of new compounds for the prevention and/or treatment of Diabetes Type 1 and 2, obesity, neuropathy and/or nephropathy.

Surprisingly we have found that N-(pyrazole-3-yl)-benzamide derivatives activate glucokinase; therefore, these compounds are especially suitable for the prevention and treatment of Diabetes Type 1 and 2, obesity, neuropathy and/or nephropathy. It has been found that the compounds according to the invention and salts thereof have very valuable pharmacological properties while being well tolerated.

In particular, they exhibit glucokinase activating effects.

The present invention therefore relates to compounds according to the invention as medicaments and/or medicament active ingredients in the treatment and/or prophylaxis of the said diseases and to the use of compounds according to the invention for the preparation of a pharmaceutical for the treatment and/or prophylaxis of the said diseases and also to a process for the treatment of the said diseases which comprises the administration of one or more compounds according to the invention to a patient in need of such an administration.

The host or patient may belong to any mammal species, for example a primate species, particularly humans; rodents, including mice, rats and hamsters; rabbits; horses, cows, dogs, cats, etc. Animal models are of interest for experimental investigations, where they provide a model for the treatment of a human disease.

Diabetes mellitus (DM) is a progressive disease often associated with obesity characterized by insulin deficiency and insulin resistance or both. The fasting and post-prandial blood glucose is elevated, exposing the patient to acute and chronic complications (micro- and macro-vascular) leading to blindness, kidney failure, heart disease, stroke and amputations. Improving glycemic control has been demonstrated to lower the risk of these complications. Owing to the progressive nature of the disease, an evolving treatment strategy is necessary to maintain glycemic control. There are two forms of diabetes mellitus: type 1, or juvenile diabetes or insulin-dependent diabetes mellitus (IDDM), and type 2, or adult-onset diabetes or non insulin-dependent diabetes mellitus (NIDDM). Type 1 diabetes patients have an absolute insulin insufficiency due to the immunological destruction of pancreatic β cells that synthesize and secrete insulin. Type 2 diabetes is more complex in etiology and is characterized by a relative insulin deficiency, reduced insulin action, and insulin resistance. Early-onset NIDDM or maturity-onset diabetes of the young (MODY) shares many features of the most common form of NIDDM whose onset occurs in the midlife (Rotter et al 1990). A clear mode of inheritance (autosomal dominant) has been observed for MODY. At least, 3 distinct mutations have been identified in MODY families (Bell et al. 1996). The importance of Glucokinase (GK) in glucose homeostasis has been demonstrated by the association of GK mutants with diabetes mellitus in humans (MODY-2) and by alteration in glucose metabolism in transgenic mice and gene knock-out mice (Froguel et al. 2003; Bali et al. 1995, Postic et al. 1999).

GK, also known as hexokinase IV or D, is one of four hexokinase isozymes that metabolize glucose to glucose 6-phosphate [Wilson, 2004]. GK is known to be expressed in neural/neuroendocrine cells, hepatocytes and pancreatic cells and plays a central role in whole body homeostasis [Matschinsky et al. 1996; 2004]. GK plays an important role as a glucose sensor for controlling plasma glucose homeostasis by enhancing insulin secretion from pancreatic β-cells and glucose metabolism in the liver but also by increasing GLP1 secretion from L-Cells. β-cells, glucose-sensing in the arcuate (ARC) hypothalamic nucleus may depend on GK to detect a rise in glucose and facilitate glucose-induced-insulin secretion.

The multiple mechanism of action of suggest that GK activators will exert their biological effects in diabetic and obese patients by improving the overall body glucose awareness which provides rational expectations that enhancement of GK activity would be a novel therapeutic strategy for metabolic disorders. It is anticipated that GK activators will restore appropriated pancreatic hormones and uncertain secretion coupled with a suppression of hepatic glucose production without inducing severe hypoglycemia.

PRIOR ART

Other benzamide derivatives are disclosed as glucokinase activators in WO 03/015774 A1, EP 1 420 784 B1, WO 2005/080359 A1, WO 2005/080360 A1, WO 2005/121110, WO 2006/040527, WO 2006/040528, WO 2006/040529, WO 2006/125972, WO 2007/007040, WO 2007/007041, WO 2007/007042, WO 2007/017649

BIBLIOGRAPHY

Wilson J E: The hexokinase gene family. In Glucokinase and Glycemic Disease: From Basics to Novel Therapeutics. Front Diabetes. Vol. 16.

Matschinsky F M, Magnuson M A, Eds. Basel, Karger, 2004

Matschinsky, F. M. Diabetes 1996, 45, 223-41.

Matschinsky F. M.; Magnuson M. A. eds. Glucokinase and Glycemic Disease: From Basics to Novel Therapeutics. Basel:Karger, 2004

Rotter et al. Diabetes mellitus (1990): Theory and practice Rifkin and Porte (Eds) NY, 378-413

Bell et al 1996

Froguel et al. 2003

Bali et al. 1995

Postic et al. 1999

SUMMARY OF THE INVENTION

The invention relates to compounds of the formula I

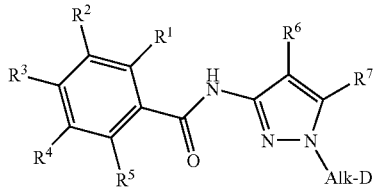

in which

| | |
|---|---|
| $R^1, R^2,$ $R^3, R^4,$ $R^5$ | each, independently of one another, denote H, A, OA, Hal, $[C(R^{12})_2]_m Ar$, $[C(R^{12})_2]_m Het$, $[C(R^{12})_2]_m O[C(R^{12})_2]_m R^{12}$, $S(O)_n R^{12}$, $NR^{10}R^{11}$, $NO_2$, CN, $COOR^{10}$, $CONR^{10}R^{11}$, $NR^{10}COR^{11}$, $NR^{10}CONR^{10}R^{11}$, $NR^{10}SO_n R^{11}$, $COR^{10}$, $SO_3H$ $SO_n NR^{10}R^{11}$, O-Alk-$NR^{10}R^{11}$, $O[C(R^{12})_2]_m CONR^{10}R^{11}$, O-Alk-$NR^{10}COR^{11}$, $O[C(R^{12})_2]_m Het$, $O[C(R^{12})_2]_m Ar$, $S(O)_n[C(R^{12})_2]_m Het$ or $S(O)_n[C(R^{12})_2]_m Ar$, |
| $R^6, R^7$ | each, independently of one another, denote H, A, $[C(R^{12})_2]_m Ar$, $[C(R^{12})_2]_m Het$, $[C(R^{12})_2]_m OCOA$, $[C(R^{12})_2]_m O[C(R^{12})_2]_m R^{12}$, $S(O)_n R^{12}$, $NR^{10}R^{11}$, CN, $COOR^{10}$, $CONR^{10}R^{11}$, $NR^{10}COR^{11}$, $NR^{10}CONR^{10}R^{11}$, $NR^{10}SO_n R^{11}$, $COR^{10}$, $SO_3H$, $SO_n NR^{10}R^{11}$, O-Alk-$NR^{10}R^{11}$, $O[C(R^{12})_2]_m CONR^{10}R^{11}$, O-Alk-$NR^{10}COR^{11}$, $O[C(R^{12})_2]_m Het$, $O[C(R^{12})_2]_m Ar$, $S(O)_n[C(R^{12})_2]_m Het$ or $S(O)_n[C(R^{12})_2]_m Ar$, |
| D | denotes Ar or Het, |
| $R^{10}, R^{11}$ | each, independently of one another, denote H, A, Ar or Het, |
| A | denotes unbranched or branched alkyl having 1-10 C atoms, in which one or two non-adjacent $CH_2$ groups may be replaced by O, S, SO, $SO_2$, NH, NA', NAr, NHet and/or by —CH=CH— groups and/or in addition 1-7 H atoms may be replaced by OH, F, Cl, Br, =S, =$NR^{12}$ and/or =O or denotes cycloalkyl having 3-7 C atoms, which is unsubstituted or mono-, di- or trisubstituted by =O, F, Cl, OH, OA', OAr', OHet', $SO_n A'$, $SO_n Ar'$, $SO_n Het'$, $NH_2$, NHA', $NA'_2$, NHAr' and/or NHHet', |
| A' | denotes unbranched or branched alkyl having 1-6 C atoms in which 1-7 H atoms may be replaced by F and/or Cl, |
| Alk | denotes unbranched or branched alkylene having 1, 2, 3 or 4 C atoms, |
| Ar | denotes phenyl, naphthyl or biphenyl, each of which is unsubstituted or mono-, di-, tri-, tetra- or pentasubstituted by A, Hal, $[C(R^{12})_2]_m Ar'$, $[C(R^{12})_2]_m Het'$, $O[C(R^{12})_2]_m R^{12}$, $S(O)_n R^{12}$, $NH_2$, NHA', $NA'_2$, NHAr', NHHet', $NO_2$, CN, $COOR^{12}$, $CON(R^{12})_2$, $NR^{12}COR^{12}$, $NR^{12}CON(R^{12})_2$, $NR^{12}SO_2 R^{12}$, $COR^{12}$, $SO_3H$, $SO_n N(R^{12})_2$, O-Alk-$N(R^{12})_2$, $O[C(R^{12})_2]_m CON(R^{12})_2$, O-Alk-$NR^{12}COR^{12}$, $O[C(R^{12})_2]_m Het'$, $O[C(R^{12})_2]_m Ar'$, $S(O)_n[C(R^{12})_2]_m Het'$ and/or $S(O)_n[C(R^{12})_2]_m Ar'$, |
| Het | denotes a mono- or bicyclic saturated, unsaturated or aromatic heterocycle having 1 to 4 N, O and/or S atoms, which may be mono-, di- or trisubstituted by Hal, A, $[C(R^{12})_2]_m Ar'$, $[C(R^{12})_2]_m Het'$, $O[C(R^{12})_2]_m Ar'$, $O[C(R^{12})_2]_m Het'$, $[C(R^{12})_2]_m$cycloalkyl, $[C(R^{12})_2]_m OR^{12}$, $[C(R^{12})_2]_m N(R^{12})_2$, $NO_2$, CN, $[C(R^{12})_2]_m COOR^{12}$, $O[C(R^{12})_2]_m COOR^{12}$, $[C(R^{12})_2]_m CON(R^{12})_2$, $[C(R^{12})_2]_m CONR^{12}N(R^{12})_2$, $O[C(R^{12})_2]_m CON(R^{12})_2$, $O[C(R^{12})_2]_m CONR^{12}N(R^{12})_2$, $[C(R^{12})_2]_m NR^{12}COA$, $NR^{12}CON(R^{12})_2$, $[C(R^{12})_2]_m NR^{12}SO_2 A$, $COR^{12}$, $SO_2 N(R^{12})_2$, $S(O)_m A$, =S, =$NR^2$ and/or =O (carbonyl oxygen), |
| Ar' | denotes phenyl, naphthyl or biphenyl, each of which is unsubstituted or mono-, di- or trisubstituted by Hal, A, $OR^{12}$, $N(R^{12})_2$, $NO_2$, CN, $COOR^{12}$, $CON(R^{12})_2$, $NR^{12}COA$, $NR^{12}CON(R^{12})_2$, $NR^{12}SO_2 A$, $COR^{12}$, $SO_2 N(R^{12})_2$, $S(O)_n A$, $[C(R^{12})_2]_m COOR^{12}$ and/or $O[C(R^{12})_2]_m COOR^{12}$, |
| Het' | denotes a mono- or bicyclic saturated, unsaturated or aromatic heterocycle having 1 to 4 N, O and/or S atoms, which may be mono-, di- or trisubstituted by Hal, A, $OR^{12}$, $N(R^{12})_2$, $NO_2$, CN, $COOR^{12}$, $CON(R^{12})_2$, $NR^{12}COA$, $NR^{12}SO_2 A$, $COR^{12}$, $SO_2 N(R^{12})_2$, $S(O)_n A$, =S, =$NR^{12}$ and/or =O (carbonyl oxygen), |
| $R^{12}$ | denotes H or unbranched or branched alkyl having 1, 2, 3, 4, 5 or 6 C atoms or denotes cycloalkyl having 3-7 C atoms, unsubstituted or monosubstituted by =O, |
| Hal | denotes F, Cl, Br or I, |
| m | denotes 0, 1, 2, 3 or 4, |
| n | denotes 0, 1 or 2, | and pharmaceutically usable salts and stereoisomers thereof, including mixtures thereof in all ratios.

The invention relates to the compounds of the formula I and salts thereof and to a process for the preparation of compounds of the formula I according to claims 1-21 and pharmaceutically usable salts and stereoisomers thereof, characterised in that a compound of the formula II

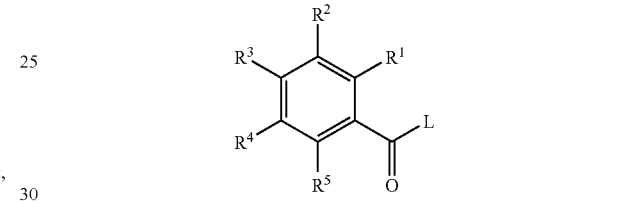

in which

L denotes Cl, Br, I or a free or reactively functionally modified OH group and $R^1, R^2, R^3, R^4$ and $R^5$ have the meanings indicated in claim 1, is reacted with a compound of the formula III

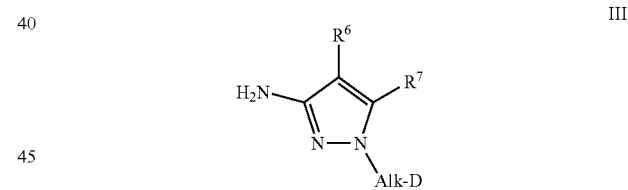

in which

Alk, D, $R^6$ and $R^7$ have the meanings indicated in claim 1, and/or a base or acid of the formula I is converted into one of its salts.

The invention also relates to the stereoisomers (E, Z isomers) and the hydrates and solvates of these compounds. Solvates of the compounds are taken to mean adductions of inert solvent molecules onto the compounds which form owing to their mutual attractive force. Solvates are, for example, mono- or dihydrates or alcoholates.

Compounds of formula I also mean their pharmaceutically usable derivatives and their solvates.

Pharmaceutically usable derivatives is taken to mean, for example, the salts of the compounds according to the invention and also so-called pro-drug compounds.

Prodrug derivatives is taken to mean compounds of the formula I which have been modified, with, for example, alkyl or acyl groups, sugars or oligopeptides and which are rapidly cleaved in the organism to form the active compounds according to the invention.

These also include biodegradable polymer derivatives of the compounds according to the invention, as is described, for example, in Int. J. Pharm. 115, 61-67 (1995).

The expression "effective amount" means the amount of a medicament or pharmaceutical active ingredient which causes a biological or medical response which is sought or aimed at, for example by a researcher or physician, in a tissue, system, animal or human.

In addition, the expression "therapeutically effective amount" means an amount which, compared with a corresponding subject who has not received this amount, has the following consequence:
improved treatment, healing, prevention or elimination of a disease, syndrome, condition, complaint, disorder or prevention of side effects or also the reduction in the progress of a disease, condition, disorder or side effects or also the reduction in the progress of a disease, condition or disorder.

The expression "therapeutically effective amount" also encompasses the amounts which are effective for increasing normal physiological function.

The invention also relates to mixtures of the compounds of the formula I according to the invention, for example mixtures of two diastereomers, for example in the ratio 1:1, 1:2, 1:3, 1:4, 1:5, 1:10, 1:100 or 1:1000. These are particularly preferably mixtures of stereoisomeric compounds.

For all radicals which occur more than once, their meanings are independent of one another.

Above and below, the radicals and parameters $R^1$, $R^2$, $R^3$, $R^4$ and D have the meanings indicated for the formula I, unless expressly indicated otherwise.

A denotes alkyl, is unbranched (linear) or branched, and has 1, 2, 3, 4, 5, 6, 7, 8, 9 or 10 C atoms. A preferably denotes methyl, furthermore ethyl, propyl, isopropyl, butyl, isobutyl, sec-butyl or tert-butyl, furthermore also pentyl, 1-, 2- or 3-methylbutyl, 1,1-, 1,2- or 2,2-dimethylpropyl, 1-ethyl-propyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl, further preferably, for example, trifluoromethyl.

A very particularly preferably denotes alkyl having 1, 2, 3, 4, 5 or 6 C atoms, preferably methyl, ethyl, propyl, isopropyl, butyl, isobutyl, sec-butyl, tert-butyl, pentyl, hexyl, trifluoromethyl, pentafluoroethyl or 1,1,1-trifluoro-ethyl.

Moreover, A preferably denotes unbranched or branched alkyl having 1-10 C atoms, in which one or two non-adjacent $CH_2$ groups may be replaced by 0 and/or in addition 1-7H atoms may be replaced by OH, F and/or Cl.

Cycloalkyl preferably denotes cyclopropyl, cyclobutyl, cyclopentyl, cyclohexyl or cycloheptyl.

Alk preferably denotes $CH_2$ order $CH_2CH_2$.

$R^1$, $R^3$, $R^5$ preferably denote H.

$R^2$, $R^4$ preferably denote each, independently of one another, OA, Hal, $[O[C(R^{12})_2]_n$Het or $O[C(R^{12})_2]_m$Ar, wherein $R^{12}$ preferably denotes H.

$R^6$, $R^7$ preferably denote each, independently of one another H or A.

$R^6$, $R^7$ particularly preferably denote each, independently of one another H or methyl, ethyl, propyl, isopropyl or butyl.

$R^{10}$, $R^{11}$ preferably denote H.

$R^{12}$ preferably denotes H or unbranched or branched alkyl having 1, 2, 3, 4, 5 or 6 C atoms, particularly preferably H or $CH_3$.

Ar denotes, for example, phenyl, o-, m- or p-tolyl, o-, m- or p-ethylphenyl, o-, m- or p-propylphenyl, o-, m- or p-isopropylphenyl, o-, m- or p-tert-butyl-phenyl, o-, m- or p-hydroxyphenyl, o-, m- or p-nitrophenyl, o-, m- or p-aminophenyl, o-, m- or p-(N-methylamino)phenyl, o-, m- or p-(N-methyl-aminocarbonyl)phenyl, o-, m- or p-acetamidophenyl, o-, m- or p-methoxy-phenyl, o-, m- or p-ethoxyphenyl, m- or p-ethoxycarbonylphenyl, o-, m- or p-(N,N-dimethylamino) phenyl, o-, m- or p-(N,N-dimethylaminocarbonyl)-phenyl, o-, m- or p-(N-ethylamino)phenyl, o-, m- or p-(N,N-diethylamino)-phenyl, o-, m- or p-fluorophenyl, o-, m- or p-bromophenyl, o-, m- or p-chlorophenyl, o-, m- or p-(methylsulfonamido)phenyl, o-, m- or p-(methyl-sulfonyl)phenyl, o-, m- or p-cyanophenyl, o-, m- or p-ureidophenyl, o-, m- or p-formylphenyl, o-, m- or p-acetylphenyl, o-, m- or p-aminosulfonyl-phenyl, o-, m- or p-carboxyphenyl, o-, m- or p-carboxymethylphenyl, o-, m- or p-carboxymethoxyphenyl, further preferably 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2,5-, 2,6-, 3,4- or 3,5-dibromophenyl, 2,4- or 2,5-dinitrophenyl, 2,5- or 3,4-dimethoxyphenyl, 3-nitro-4-chlorophenyl, 3-amino-4-chloro-, 2-amino-3-chloro-, 2-amino-4-chloro-, 2-amino-5-chloro- or 2-amino-6-chlorophenyl, 2-nitro-4-N,N-dimethylamino- or 3-nitro-4-N,N-dimethylaminophenyl, 2,3-diaminophenyl, 2,3,4-, 2,3,5-, 2,3,6-, 2,4,6- or 3,4,5-trichlorophenyl, 2,4,6-trimethoxyphenyl, 2-hydroxy-3,5-dichlorophenyl, p-iodophenyl, 3,6-dichloro-4-aminophenyl, 4-fluoro-3-chlorophenyl, 2-fluoro-4-bromophenyl, 2,5-difluoro-4-bromophenyl, 3-bromo-6-methoxyphenyl, 3-chloro-6-methoxyphenyl, 3-chloro-4-acetamidophenyl, 3-fluoro-4-methoxyphenyl, 3-amino-6-methylphenyl, 3-chloro-4-acetamidophenyl or 2,5-dimethyl-4-chlorophenyl.

Ar preferably denotes, for example, phenyl which is unsubstituted or monosubstituted by $SO_nNR^{12}$, preferably methylaminosulfonyl; by $SO_nA$, preferably, $SO_2CH_3$; by CONHA, CODA, COOH, $CH_2COOH$ or $CH_2COOH$. Ar very particularly preferably is phenyl which is unsubstituted.

Ar' preferably denotes, for example, phenyl which is unsubstituted or mono-, di- or trisubstituted by Hal, A, OH, OA, $SO_2A$, COOA or CN, very particularly preferably phenyl which is unsubstituted or mono-, di- or trisubstituted by Hal and/or A.

Irrespective of further substitutions, Het denotes, for example, 2- or 3-furyl, 2- or 3-thienyl, 1-, 2- or 3-pyrrolyl, 1-, 2,4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, furthermore preferably 1,2,3-triazol-1-,-4- or -5-yl, 1,2,4-triazol-1-,-3- or 5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 3- or 4-pyridazinyl, pyrazinyl, 1-, 2-, 3-, 4-, 5-, 6- or 7-indolyl, 4- or 5-isoindolyl, 1-, 2-, 4- or 5-benzimidazolyl, 1-, 2-, 3-, 4-, 5-, 6- or 7-indazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 2-, 3-, 4-, 5-, 6-, 7- or 8-quinolyl, 1-, 3-, 4-, 5-, 6-, 7- or 8-isoquinolyl, 3-, 4-, 5-, 6-, 7- or 8-innolinyl, 2-, 4-, 5-, 6-, 7- or 8-quinazolinyl, 5- or 6-quinoxalinyl, 2-, 3-, 5-, 6-, 7- or 8-2H-benzo-1,4-oxazinyl, further preferably 1,3-benzodioxol-5-yl, 1,4-benzodioxan-6-yl, 2,1,3-benzothiadiazol-4- or -5-yl or 2,1,3-benzoxadiazol-5-yl.

The heterocyclic radicals can also be partially or fully hydrogenated. Het can thus also denote, for example, 2,3-dihydro-2-,-3-,-4- or -5-furyl, 2,5-dihydro-2-,-3-,-4- or 5-furyl, tetrahydro-2- or -3-furyl, 1,3-dioxolan-4-yl, tetrahydro-2- or -3-thienyl, 2,3-dihydro-1-,-2-,-3-,-4- or -5-pyrrolyl, 2,5-di-hydro-1-,-2-,-3-,-4- or -5-pyrrolyl, 1-, 2- or 3-pyrrolidinyl, tetrahydro-1-,-2- or -4-imidazolyl, 2,3-dihydro-1-,-2-,-3-, A- or -5-pyrazolyl, tetrahydro-1-,-3- or -4-pyrazolyl, 1,4-dihydro-1-,-2-,-3- or -4-pyridyl, 1,2,3,4-tetrahydro-1-,-2-,-3-,-4-,-5- or -6-pyridyl, 1-, 2-, 3- or 4-piperidinyl, 2-, 3- or 4-morpholinyl, tetrahydro-2-,-3- or -4-pyranyl, 1,4-dioxanyl, 1,3-dioxan-2-,-4- or -5-yl, hexahydro-1-,-3- or -4-pyridazinyl, hexahydro-1-,-2-,-4- or -5-pyrimidinyl, 1-, 2- or 3-piperazinyl, 1,2,3,4-tetrahydro-1-,-2-,-3-,-4-,-5-,-6-,-7- or -8-quinolyl, 1,2,3,4-tetrahydro-1-,-2-,-3-,-4-,-5-,-6-,-7- or -8-isoquinolyl, 2-, 3-, 5-, 6-, 7- or 8-3,4-dihydro-2H-benzo-1,4-oxazinyl, further preferably 2,3-methylenedioxyphenyl, 3,4-methylenedioxyphenyl, 2,3-ethylenedioxy-phenyl, 3,4-ethylenedioxyphenyl, 3,4-(difluoromethylenedioxy)phenyl, 2,3-dihydrobenzofuran-5- or 6-yl, 2,3-(2-oxomethylenedioxy)phenyl or also 3,4-dihydro-2H-1,5-benzodioxepin-6- or -7-yl, furthermore preferably 2,3-dihydrobenzofuranyl or 2,3-dihydro-2-oxofuranyl.

Het preferably denotes a monocyclic saturated, unsaturated or aromatic heterocycle having 1 to 4 N, O and/or S atoms, which may be monosubstituted by A, $[C(R^{12})_2]_m CON(R^{12})_2$ and/or =O (carbonyl oxygen). Het particularly preferably denotes furyl, thienyl, pyrrolyl, imidazolyl, pyridyl, pyrimidinyl, pyrazolyl, thiazolyl, pyrrolidinyl, piperidinyl, morpholinyl, tetrahydropyranyl or piperazinyl, each of which is unsubstituted or monosubstituted by A, $[C(R^{12})_2]_m CON(R^{12})_2$ and/or =O (carbonyl oxygen), wherein $[C(R^{12})_2]_m CON(R^{12})_2$ preferably denotes $CONH_2$, $CONHCH_3$ or $CON(CH_3)_2$.

Het' preferably denotes a monocyclic saturated, unsaturated or aromatic heterocycle having 1 to 2 N and/or O atoms, which may be unsubstituted or mono-, di- or trisubstituted by A, Hal, OH and/or OA.

Het' particularly preferably denotes a monocyclic saturated heterocycle having 1 to 2 N and/or O atoms, which may be unsubstituted or mono- or disubstituted by A.

In a further embodiment, Het' very particularly denotes pyrrolidinyl, piperidinyl, morpholinyl or piperazinyl.

In a further embodiment, Het' particularly preferably denotes furyl, thienyl, pyrrolyl, imidazolyl, pyridyl, pyrimidinyl, pyrazolyl, thiazolyl, indolyl, pyrrolidinyl, piperidinyl, morpholinyl or piperazinyl, each of which is unsubstituted or mono-, di- or trisubstituted by A, Hal, OH and/or OA.

Mono- or bicyclic saturated, unsaturated or aromatic heterocycle denotes, for example, 2- or 3-furyl, 2- or 3-thienyl, 1-, 2- or 3-pyrrolyl, 1-, 2,4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, furthermore preferably 1,2,3-triazol-1-,-4- or -5-yl, 1,2,4-triazol-1-,-3- or 5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 3- or 4-pyridazinyl, pyrazinyl, 1-, 2-, 3-, 4-, 5-, 6- or 7-indolyl, 4- or 5-isoindolyl, 1-, 2-, 4- or 5-benzimidazolyl, 1-, 2-, 3-, 4-, 5-, 6- or 7-indazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 2-, 3-, 4-, 5-, 6-, 7- or 8-quinolyl, 1-, 3-, 4-, 5-, 6-, 7- or 8-isoquinolyl, 3-, 4-, 5-, 6-, 7- or 8-cinnolinyl, 2-, 4-, 5-, 6-, 7- or 8-quinazolinyl, 5- or 6-quinoxalinyl, 2-, 3-, 5-, 6-, 7- or 8-2H-benzo-1,4-oxazinyl, further preferably 1,3-benzodioxol-5-yl, 1,4-benzodioxan-6-yl, 2,1,3-benzothiadiazol-4- or -5-yl or 2,1,3-benzoxadiazol-5-yl, furthermore 2,3-dihydro-2-,-3-,-4- or -5-furyl, 2,5-dihydro-2-,-3-,-4- or 5-furyl, tetrahydro-2- or -3-furyl, 1,3-dioxolan-4-yl, tetrahydro-2- or -3-thienyl, 2,3-dihydro-1-,-2-,-3-,-4- or -5-pyrrolyl, 2,5-dihydro-1-,-2-,-3-,-4- or -5-pyrrolyl, 1-, 2- or 3-pyrrolidinyl, tetrahydro-1-,-2- or -4-imidazolyl, 2,3-dihydro-1-,-2-,-3-,-4- or -5-pyrazolyl, tetrahydro-1-,-3- or -4-pyrazolyl, 1,4-dihydro-1-,-2-,-3- or -4-pyridyl, 1,2,3,4-tetrahydro-1-,-2-,-3-,-4-,-5- or -6-pyridyl, 1-, 2-, 3- or 4-piperidinyl, 2-, 3- or 4-morpholinyl, tetrahydro-2-,-3- or -4-pyranyl, 1,4-dioxanyl, 1,3-dioxan-2-,-4- or -5-yl, hexahydro-1-,-3- or -4-pyridazinyl, hexahydro-1-,-2-,-4- or -5-pyrimidinyl, 1-, 2- or 3-piperazinyl, 1,2,3,4-tetrahydro-1-,-2-,-3-,-4-,-5-,-6-,-7- or -8-quinolyl, 1,2,3,4-tetrahydro-1-,-2-,-3-,-4-,-5-,-6-,-7- or -8-isoquinolyl, 2-, 3-, 5-, 6-, 7- or 8-3,4-dihydro-2H-benzo-1,4-oxazinyl, 2,3-methylenedioxyphenyl, 3,4-methylenedioxyphenyl, 2,3-ethylenedioxyphenyl, 3,4-ethylenedioxyphenyl, 3,4-(difluoromethylenedioxy)phenyl, 2,3-dihydrobenzofuran-5- or 6-yl, 2,3-(2-oxomethylenedioxy)phenyl or also 3,4-dihydro-2H-1,5-benzodioxepin-6- or -7-yl, furthermore 2,3-dihydrobenzofuranyl or 2,3-dihydro-2-oxofuranyl.

The compounds of the formula I may have one or more chiral centres and can therefore occur in various stereoisomeric forms. The formula I encompasses all these forms.

Accordingly, the invention relates, in particular, to the compounds of the formula I in which at least one of the said radicals has one of the preferred meanings indicated above. Some preferred groups of compounds may be expressed by the following sub-formulae Ia to Ij, which conform to the formula I and in which the radicals not designated in greater detail have the meaning indicated for the formula I, but in which

| in Ia | $R^1, R^3, R^5$ | denote H; |
|---|---|---|
| in Ib | $R^2, R^4$ | denote each, independently of one another, OA, Hal, $[O[C(R^{12})_2]_m$Het or $O[C(R^{12})_2]_m$Ar; |
| in Ic | $R^6, R^7$ | each, independently of one another, denote H or A; |
| in Id | A | denotes unbranched or branched alkyl having 1-10 C atoms, in which one or two non-adjacent $CH_2$ groups may be replaced by O and/or in addition 1-7 H atoms may be replaced by OH, F and/or Cl; |
| in Ie | Ar | denotes denotes phenyl which is unsubstituted or monosubstituted by $SO_nR^{12}$, |
| in If | Het | denotes a monocyclic saturated, unsaturated or aromatic heterocycle having 1 to 4 N, O and/or S atoms, which may be monosubstituted by $[C(R^{12})_2]_m CON(R^{12})_2$, A or =O (carbonyl oxygen); |
| in Ig | Het | denotes furyl, thienyl, pyrrolyl, imidazolyl, pyridyl, pyrimidinyl, pyrazolyl, thiazolyl, pyrrolidinyl, piperidinyl, morpholinyl, tetrahydropyranyl or piperazinyl, each of which is unsubstituted or monosubstituted by $[C(R^{12})_2]_m CON(R^{12})_2$, A or =O (carbonyl oxygen); |
| in Ih | $R^{12}$ | denotes H or unbranched or branched alkyl having 1, 2, 3, 4, 5 or 6 C atoms; |
| in Ii | $R^1, R^3, R^5$ | denote H, |
| | $R^2, R^4$ | denote each, independently of one another, OA, Hal, $[O[C(R^{12})_2]_m$Het or $O[C(R^{12})_2]_m$Ar, |
| | $R^6, R^7$ | denote each, independently of one another, H or A, |
| | D | denotes Ar or Het, |
| | A | denotes unbranched or branched alkyl having 1-10 C atoms, in which one or two non-adjacent $CH_2$ groups may be replaced by O and/or in addition 1-7 H atoms may be replaced by OH, F and/or Cl, |
| | Alk | denotes unbranched or branched alkylene having 1, 2, 3 or 4 C atoms, |
| | Ar | denotes denotes phenyl which is unsubsituted or monosubstituted by $SO_nR^{12}$, |
| | Het | denotes a monocyclic saturated, unsaturated or aromatic heterocycle having 1 to 4 N, O and/or S atoms, which may be monosubstituted by $[C(R^{12})_2]_m CON(R^{12})_2$, A or =O (carbonyl oxygen), |
| | $R_{12}$ | denotes H or unbranched or branched alkyl having 1, 2, 3, 4, 5 or 6 C atoms, |

-continued

| | | |
|---|---|---|
| | Hal | denotes F, Cl, Br or I, |
| | m | denotes 0, 1, 2, 3 or 4, |
| | n | denotes 0, 1 or 2; |
| in Ij | $R^1$, $R^3$, $R^5$ | denote H, |
| | $R^2$, $R^4$ | denote each, independently of one another, OA, Hal, $[O[C(R^{12})_2]_m$Het or $O[C(R^{12})_2]_m$Ar, |
| | $R^6$, $R^7$ | denote each, independently of one another, H or A, |
| | D | denotes Ar or Het, |
| | A | denotes unbranched or branched alkyl having 1-10 C atoms, in which one or two non-adjacent $CH_2$ groups may be replaced by O and/or in addition 1-7 H atoms may be replaced by OH, F and/or Cl, |
| | Alk | denotes unbranched or branched alkylene having 1, 2, 3 or 4 C atoms, |
| | Ar | denotes phenyl which is unsubstituted or monosubstituted by $SO_nR^{12}$, |
| | Het | denotes furyl, thienyl, pyrrolyl, imidazolyl, pyridyl, pyrimidinyl, pyrazolyl, thiazolyl, pyrrolidinyl, piperidinyl, morpholinyl, tetrahydropyranyl or piperazinyl, each of which is unsubstituted or monosubstituted by $[C(R^{12})_2]_m CON(R^{12})_2$, A or =O (carbonyl oxygen), |
| | $R^{12}$ | denotes H or unbranched or branched alkyl having 1, 2, 3, 4, 5 or 6 C atoms, |
| | Hal | denotes F, Cl, Br or I, |
| | m | denotes 0, 1, 2, 3 or 4, |
| | n | denotes 0, 1 or 2; | and pharmaceutically usable salts and stereoisomers thereof, including mixtures thereof in all ratios.

The compounds according to the invention and also the starting materials for their preparation are, in addition, prepared by methods known per se, as described in the literature (for example in the standard works, such as Houben-Weyl, Methoden der organischen Chemie [Methods of Organic Chemistry], Georg-Thieme-Verlag, Stuttgart), to be precise under reaction conditions which are known and suitable for the said reactions. Use can also be made here of variants known per se, which are not mentioned here in greater detail.

If desired, the starting materials can also be formed in situ so that they are not isolated from the reaction mixture, but instead are immediately converted further into the compounds according to the invention.

The starting compounds are generally known. If they are novel, however, they can be prepared by methods known per se.

Compounds of the formula I, can preferably be obtained by reacting a compound of the formula II with a compound of the formula III.

The reaction is carried out by methods which are known to the person skilled in the art.

The reaction is generally carried out in an inert solvent, in the presence of an acid-binding agent, preferably an alkali or alkaline-earth metal hydroxide, carbonate or bicarbonate or another salt of a weak acid of the alkali or alkaline-earth metals, preferably of potassium, sodium, calcium or caesium. The addition of an organic base, such as triethylamine, dimethyl-aniline, pyridine or quinoline may also be favourable.

The starting substances of the formulae II and III are known in some cases. If they are not known, they can be prepared by methods known per se.

In the compounds of the formula II, L is preferably Cl, Br, I or a free or reactively modified OH group, such as, for example, an activated ester, an imidazolide or alkylsulfonyloxy having 1-6 carbon atoms (preferably methylsulfonyloxy or trifluoromethylsulfonyloxy) or arylsulfonyloxy having 6-10 carbon atoms (preferably phenyl- or p-tolylsulfonyloxy).

Radicals of this type for activation of the carboxyl group in typical acylation reactions are described in the literature (for example in the standard works, such as Houben-Weyl, Methoden der organischen Chemie [Methods of Organic Chemistry], Georg-Thieme-Verlag, Stuttgart).

Activated esters are advantageously formed in situ, for example through addition of HOBt or N-hydroxysuccinimide.

Suitable inert solvents are for example, hydrocarbons, such as hexane, petroleum ether, benzene, toluene or xylene; chlorinated hydrocarbons, such as trichloroethylene, 1,2-dichloroethane, carbon tetrachloride, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether, ethylene glycol dimethyl ether (diglyme); ketones, such as acetone or butanone; amides, such as acetamide, dimethylacetamide or dimethylformamide (DMF); nitriles, such as acetonitrile; sulfoxides, such as dimethyl sulfoxide (DMSO); carbon disulfide; carboxylic acids, such as formic acid or acetic acid; nitro compounds, such as nitromethane or nitrobenzene; esters, such as ethyl acetate, or mixtures of the said solvents.

Depending on the conditions used, the reaction time is between a few minutes and 14 days, the reaction temperature is between about −30° and 140°, normally between −10° and 110°, in particular between about 20° and about 100°.

Other radicals can be converted by reducing nitro groups (for example by hydrogenation on Raney nickel or Pd/carbon in an inert solvent, such as methanol or ethanol) to amino groups or hydrolysing cyano groups to COON groups.

Furthermore, free amino groups can be acylated in a conventional manner using an acid chloride or anhydride or alkylated using an unsubstituted or substituted alkyl halide, advantageously in an inert solvent, such as dichloromethane or THF, and/or in the presence of a base, such as triethylamine or pyridine, at temperatures between −60 and +30°. Ester groups can be saponified, for example, using NaOH or KOH in water, water/THF or water/dioxane at temperatures between 0 and 100°. Carboxylic acids can be converted, for example using thionyl chloride, into the corresponding carboxylic acid chlorides, and the latter can be converted into carboxamides. Elimination of water therefrom in a known manner gives carbonitriles.

Pharmaceutical Salts and Other Forms

The said compounds according to the invention can be used in their final non-salt form. On the other hand, the present invention also encompasses the use of these compounds in the form of their pharmaceutically acceptable salts, which can be derived from various organic and inorganic acids and bases by procedures known in the art. Pharmaceutically acceptable salt forms of the compounds of the formula I are for the most part prepared by conventional methods. If the compound of the formula I contains a carboxyl group, one of its suitable salts can be formed by reacting the compound with a suitable base to give the corresponding base-addition salt. Such bases are, for example, alkali metal hydroxides, including potassium hydroxide, sodium hydroxide and lithium hydroxide; alkaline earth metal hydroxides, such as barium hydroxide and calcium hydroxide; alkali metal alkoxides, for example potassium ethoxide and sodium propoxide; and various organic bases, such as piperidine, diethanolamine and N-methyl-glutamine. The aluminium salts of the compounds of the formula I are like-wise included. In the case of certain compounds of the formula I, acid-addition salts can be formed by treating these compounds with pharmaceutically acceptable organic and inorganic acids, for example hydrogen halides, such as hydrogen chloride; hydrogen bromide or hydrogen iodide, other mineral acids and corresponding salts thereof, such as sulfate, nitrate or phosphate and the like, and alkyl- and monoarylsulfonates, such as ethanesulfonate, toluenesulfonate and benzenesulfonate, and other organic acids and corresponding salts thereof, such as acetate, trifluoroacetate, tartrate, maleate, succinate, citrate, benzoate, salicylate, ascorbate and the like. Accordingly, pharmaceutically acceptable acid-addition salts of the compounds of the formula I include the following: acetate, adipate, alginate, arginate, aspartate, benzoate, benzenesulfonate (besylate), bisulfate, bisulfite, bromide, butyrate, camphorate, camphorsulfonate, caprylate, chloride, chlorobenzoate, citrate, cyclopentanepropionate, digluconate, dihydrogenphosphate, dinitrobenzoate, dodecylsulfate, ethanesulfonate, fumarate, galacterate (from mucic acid), galacturonate, glucoheptanoate, gluconate, glutamate, glycerophosphate, hemisuccinate, hemisulfate, heptanoate, hexanoate, hippurate, hydrochloride, hydrobromide, hydroiodide, 2-hydroxyethanesulfonate, iodide, isethionate, isobutyrate, lactate, lactobionate, malate, maleate, malonate, mandelate, metaphosphate, methanesulfonate, methylbenzoate, monohydrogenphosphate, 2-naphthalenesulfonate, nicotinate, nitrate, oxalate, oleate, palmoate, pectinate, persulfate, phenylacetate, 3-phenylpropionate, phosphate, phosphonate, phthalate, but this does not represent a restriction.

Furthermore, the base salts of the compounds according to the invention include aluminium, ammonium, calcium, copper, iron(III), iron(II), lithium, magnesium, manganese(III), manganese(II), potassium, sodium and zinc salts, but this is not intended to represent a restriction. Of the above-mentioned salts, preference is given to ammonium; the alkali metal salts sodium and potassium, and the alkaline earth metal salts calcium and magnesium. Salts of the compounds of the formula I which are derived from pharmaceutically acceptable organic non-toxic bases include salts of primary, secondary and tertiary amines, substituted amines, also including naturally occurring substituted amines, cyclic amines, and basic ion exchanger resins, for example arginine, betaine, caffeine, chloroprocaine, choline, N,N'-dibenzylethylenediamine(benzathine), dicyclohexylamine, diethanolamine, diethylamine, 2-diethylaminoethanol, 2-dimethylamino-ethanol, ethanolamine, ethylenediamine, N-ethylmorpholine, N-ethylpiperidine, glucamine, glucosamine, histidine, hydrabamine, isopropylamine, lidocaine, lysine, meglumine, N-methyl-D-glucamine, morpholine, piperazine, piperidine, polyamine resins, procaine, purines, theobromine, triethanolamine, triethylamine, trimethylamine, tripropylamine and tris-hydroxymethyl)methylamine (tromethamine), but this is not intended to represent a restriction.

Compounds of the present invention which contain basic nitrogen-containing groups can be quaternised using agents such as $(C_1-C_4)$alkyl halides, for example methyl, ethyl, isopropyl and tert-butyl chloride, bromide and iodide; $di(C_1-C_4)$ alkyl sulfates, for example dimethyl, diethyl and diamyl sulfate; $(C_{10}-C_{18})$alkyl halides, for example decyl, dodecyl, lauryl, myristyl and stearyl chloride, bromide and iodide; and aryl$(C_1-C_4)$alkyl halides, for example benzyl chloride and phenethyl bromide. Both water- and oil-soluble compounds according to the invention can be prepared using such salts.

The above-mentioned pharmaceutical salts which are preferred include acetate, trifluoroacetate, besylate, citrate, fumarate, gluconate, hemisuccinate, hippurate, hydrochloride, hydrobromide, isethionate, mandelate, meglumine, nitrate, oleate, phosphonate, pivalate, sodium phosphate, stearate, sulfate, sulfosalicylate, tartrate, thiomalate, tosylate and tromethamine, but this is not intended to represent a restriction.

The acid-addition salts of basic compounds of the formula I are prepared by bringing the free base form into contact with a sufficient amount of the desired acid, causing the formation of the salt in a conventional manner. The free base can be regenerated by bringing the salt form into contact with a base and isolating the free base in a conventional manner. The free base forms differ in a certain respect from the corresponding salt forms thereof with respect to certain physical properties, such as solubility in polar solvents; for the purposes of the invention, however, the salts otherwise correspond to the respective free base forms thereof.

As mentioned, the pharmaceutically acceptable base-addition salts of the compounds of the formula I are formed with metals or amines, such as alkali metals and alkaline earth metals or organic amines. Preferred metals are sodium, potassium, magnesium and calcium. Preferred organic amines are N,N'-dibenzylethylenediamine, chloroprocaine, choline, diethanolamine, ethylenediamine, N-methyl-D-glucamine and procaine.

The base-addition salts of acidic compounds according to the invention are prepared by bringing the free acid form into contact with a sufficient amount of the desired base, causing the formation of the salt in a conventional manner. The free acid can be regenerated by bringing the salt form into contact with an acid and isolating the free acid in a conventional manner. The free acid forms differ in a certain respect from the corresponding salt forms thereof with respect to certain physical properties, such as solubility in polar solvents; for the purposes of the invention, however, the salts otherwise correspond to the respective free acid forms thereof.

If a compound according to the invention contains more than one group which is capable of forming pharmaceutically acceptable salts of this type, the invention also encompasses multiple salts. Typical multiple salt forms include, for example, bitartrate, diacetate, difumarate, dimeglumine, diphosphate, disodium and trihydrochloride, but this is not intended to represent a restriction.

With regard to that stated above, it can be seen that the expression "pharmaceutically acceptable salt" in the present connection is taken to mean an active ingredient which comprises a compound of the formula I in the form of one of its salts, in particular if this salt form imparts improved pharmacokinetic properties on the active ingredient compared with the free form of the active ingredient or any other salt form of the active ingredient used earlier. The pharmaceutically acceptable salt form of the active ingredient can also provide this active ingredient for the first time with a desired pharmacokinetic property which it did not have earlier and can even have a positive influence on the pharmacodynamics of this active ingredient with respect to its therapeutic efficacy in the body.

Compounds of the formula I according to the invention may be chiral owing to their molecular structure and may accordingly occur in various enantiomeric forms. They can therefore exist in racemic or in optically active form.

Since the pharmaceutical activity of the racemates or stereoisomers of the compounds according to the invention may differ, it may be desirable to use the enantiomers. In these cases, the end product or even the intermediates can be separated into enantiomeric compounds by chemical or physical measures known to the person skilled in the art or even employed as such in the synthesis.

In the case of racemic amines, diastereomers are formed from the mixture by reaction with an optically active resolving agent. Examples of suitable resolving agents are optically active acids, such as the R and S forms of tartaric acid, diacetyltartaric acid, dibenzoyltartaric acid, mandelic acid, malic acid, lactic acid, suitably N-protected amino acids (for example N-benzoylproline or N-benzenesulfonylproline), or the various optically active camphorsulfonic acids. Also advantageous is chromatographic enantiomer resolution with the aid of an optically active resolving agent (for example dinitrobenzoylphenylglycine, cellulose triacetate or other derivatives of carbohydrates or chirally derivatised methacrylate polymers immobilised on silica gel). Suitable eluents for this purpose are aqueous or alcoholic solvent mixtures, such as, for example, hexane/isopropanol/acetonitrile, for example in the ratio 82:15:3.

The invention furthermore relates to the use of the compounds and/or physiologically acceptable salts thereof for the preparation of a medicament (pharmaceutical composition), in particular by non-chemical methods. They can be converted into a suitable dosage form here together with at least one solid, liquid and/or semi-liquid excipient or adjuvant and, if desired; in combination with one or more further active ingredients.

The invention furthermore relates to medicaments comprising at least one compound according to the invention and/or pharmaceutically usable derivatives, solvates and stereoisomers thereof, including mixtures thereof in all ratios, and optionally excipients and/or adjuvants.

Pharmaceutical formulations can be administered in the form of dosage units which comprise a predetermined amount of active ingredient per dosage unit. Such a unit can comprise, for example, 0.5 mg to 1 g, preferably 1 mg to 700 mg, particularly preferably 5 mg to 100 mg, of a corn-pound according to the invention, depending on the disease condition treated, the method of administration and the age, weight and condition of the patient, or pharmaceutical formulations can be administered in the form of dosage units which comprise a predetermined amount of active ingredient per dosage unit. Preferred dosage unit formulations are those which comprise a daily dose or part-dose, as indicated above, or a corresponding fraction thereof of an active ingredient. Furthermore, pharmaceutical formulations of this type can be prepared using a process which is generally known in the pharmaceutical art.

Pharmaceutical formulations can be adapted for administration via any desired suitable method, for example by oral (including buccal or sublingual), rectal, nasal, topical (including buccal, sublingual or transdermal), vaginal or parenteral (including subcutaneous, intramuscular, intravenous or intradermal) methods. Such formulations can be prepared using all processes known in the pharmaceutical art by, for example, combining the active ingredient with the excipient(s) or adjuvant(s).

Pharmaceutical formulations adapted for oral administration can be administered as separate units, such as, for example, capsules or tablets; powders or granules; solutions or suspensions in aqueous or non-aqueous liquids; edible foams or foam foods; or oil-in-water liquid emulsions or water-in-oil liquid emulsions.

Thus, for example, in the case of oral administration in the form of a tablet or capsule, the active-ingredient component can be combined with an oral, non-toxic and pharmaceutically acceptable inert excipient, such as, for example, ethanol, glycerol, water and the like. Powders are prepared by comminuting the compound to a suitable fine size and mixing it with a pharmaceutical excipient comminuted in a similar manner, such as, for example, an edible carbohydrate, such as, for example, starch or mannitol. A flavour, preservative, dispersant and dye may likewise be present.

Capsules are produced by preparing a powder mixture as described above and filling shaped gelatine shells therewith. Glidants and lubricants, such as, for example, highly disperse silicic acid, talc, magnesium stearate, calcium stearate or polyethylene glycol in solid form, can be added to the powder mixture before the filling operation. A disintegrant or solubiliser, such as, for example, agar-agar, calcium carbonate or sodium carbonate, may likewise be added in order to improve the availability of the medicament after the capsule has been taken.

In addition, if desired or necessary, suitable binders, lubricants and disintegrants as well as dyes can likewise be incorporated into the mixture. Suitable binders include starch, gelatine, natural sugars, such as, for example, glucose or beta-lactose, sweeteners made from maize, natural and synthetic rubber, such as, for example, acacia, tragacanth or sodium alginate, carboxymethylcellulose, polyethylene glycol, waxes, and the like. The lubricants used in these dosage forms include sodium oleate, sodium stearate, magnesium stearate, sodium benzoate, sodium acetate, sodium chloride and the like. The disintegrants include, without being restricted thereto, starch, methylcellulose, agar, bentonite, xanthan gum and the like.

The tablets are formulated by, for example, preparing a powder mixture, granulating or dry-pressing the mixture, adding a lubricant and a disintegrant and pressing the entire mixture to give tablets. A powder mixture is prepared by mixing the compound comminuted in a suitable manner with a diluent or a base, as described above, and optionally with a binder, such as, for example, carboxymethylcellulose, an alginate, gelatine or polyvinyl-pyrrolidone, a dissolution retardant, such as, for example, paraffin, an absorption accelerator, such as, for example, a quaternary salt, and/or an absorbent, such as, for example, bentonite, kaolin or dicalcium phosphate. The powder mixture can be granulated by wetting it with a binder, such as, for example, syrup, starch paste, acadia mucilage or solutions of cellulose or polymer materials and pressing it through a sieve. As an alternative to granulation, the powder mixture can be run through a tableting machine, giving lumps of nonuniform shape which are broken u to form granules. The granules can be lubricated by addition of stearic acid, a stearate salt, talc or mineral oil in order to prevent sticking to the tablet casting moulds. The lubricated mixture is then pressed to give tablets. The compounds according to the invention can also be combined with a free-flowing inert excipient and then pressed directly to give tablets without carrying out the granulation or dry-pressing steps. A transparent or opaque protective layer consisting of a shellac sealing layer, a layer of sugar or polymer material and a gloss layer of wax may be present. Dyes can be added to these coatings in order to be able to differentiate between different dosage units.

Oral liquids, such as, for example, solution, syrups and elixirs, can be prepared in the form of dosage units so that a given quantity comprises a pre-specified amount of the compounds. Syrups can be prepared by dissolving the compound in an aqueous solution with a suitable flavour, while elixirs are prepared using a non-toxic alcoholic vehicle. Suspensions can be formulated by dispersion of the compound in a non-toxic vehicle. Solubilisers and emulsifiers, such as, for example, ethoxylated isostearyl alcohols and polyoxyethylene sorbitol ethers, preservatives, flavour additives, such as, for example, peppermint oil or natural sweeteners or saccharin, or other artificial sweeteners and the like, can likewise be added.

The dosage unit formulations for oral administration can, if desired, be en-capsulated in microcapsules. The formulation can also be prepared in such a way that the release is extended or retarded, such as, for example, by coating or embedding of particulate material in polymers, wax and the like.

The compounds according to the invention and salts, solvates and physiologically functional derivatives thereof can also be administered in the form of liposome delivery systems, such as, for example, small unilamellar vesicles, large unilamellar vesicles and multilamellar vesicles. Liposomes can be formed from various phospholipids, such as, for example, cholesterol, stearylamine or phosphatidyicholines.

The compounds according to the invention and the salts, solvates and physiologically functional derivatives thereof can also be delivered using monoclonal antibodies as individual carriers to which the compound molecules are coupled. The compounds can also be coupled to soluble polymers as targeted medicament carriers. Such polymers may encompass polyvinylpyrrolidone, pyran copolymer, polyhydroxypropylmethacrylamidophenol, polyhydroxyethylaspartamidophenol or polyethylene oxide polylysine, substituted by palmitoyl radicals. The compounds may furthermore be coupled to a class of biodegradable polymers which are suitable for achieving controlled release of a medicament, for example polylactic acid, poly-epsilon-caprolactone, polyhydroxybutyric acid, polyorthoesters, polyacetals, polydihydroxypyrans, polycyanoacrylates and crosslinked or amphipathic block copolymers of hydrogels.

Pharmaceutical formulations adapted for transdermal administration can be administered as independent plasters for extended, close contact with the epidermis of the recipient. Thus, for example, the active ingredient can be delivered from the plaster by iontophoresis, as described in general terms in Pharmaceutical Research, 3(6), 318 (1986).

Pharmaceutical compounds adapted for topical administration can be formulated as ointments, creams, suspensions, lotions, powders, solutions, pastes, gels, sprays, aerosols or oils.

For the treatment of the eye or other external tissue, for example mouth and skin, the formulations are preferably applied as topical ointment or cream. In the case of formulation to give an ointment, the active ingredient can be employed either with a paraffinic or a water-miscible cream base. Alternatively, the active ingredient can be formulated to give a cream with an oil-in-water cream base or a water-in-oil base.

Pharmaceutical formulations adapted for topical application to the eye include eye drops, in which the active ingredient is dissolved or suspended in a suitable carrier, in particular an aqueous solvent.

Pharmaceutical formulations adapted for topical application in the mouth encompass lozenges, pastilles and mouthwashes.

Pharmaceutical formulations adapted for rectal administration can be administered in the form of suppositories or enemas.

Pharmaceutical formulations adapted for nasal administration in which the carrier substance is a solid comprise a coarse powder having a particle size, for example, in the range 20-500 microns, which is administered in the manner in which snuff is taken, i.e. by rapid inhalation via the nasal passages from a container containing the powder held close to the nose. Suitable formulations for administration as nasal spray or nose drops with a liquid as carrier substance encompass active-ingredient solutions in water or oil.

Pharmaceutical formulations adapted for administration by inhalation en-compass finely particulate dusts or mists, which can be generated by various types of pressurised dispensers with aerosols, nebulisers or insufflators.

Pharmaceutical formulations adapted for vaginal administration can be administered as pessaries, tampons, creams, gels, pastes, foams or spray formulations.

Pharmaceutical formulations adapted for parenteral administration include aqueous and non-aqueous sterile injection solutions comprising antioxidants, buffers, bacteriostatics and solutes, by means of which the formulation is rendered isotonic with the blood of the recipient to be treated; and aqueous and non-aqueous sterile suspensions, which may comprise suspension media and thickeners. The formulations can be administered in single-dose or multidose containers, for example sealed ampoules and vials, and stored in freeze-dried (lyophilised) state, so that only the addition of the sterile carrier liquid, for example water for injection purposes, immediately before use is necessary.

Injection solutions and suspensions prepared in accordance with the recipe can be prepared from sterile powders, granules and tablets.

It goes without saying that, in addition to the above particularly mentioned constituents, the formulations may also comprise other agents usual in the art with respect to the particular type of formulation; thus, for example, formulations which are suitable for oral administration may comprise flavours.

A therapeutically effective amount of a compound of the present invention depends on a number of factors, including, for example, the age and weight of the human or animal, the precise disease condition which requires treatment, and its severity, the nature of the formulation and the method of administration, and is ultimately determined by the treating doctor or vet. However, an effective amount of a compound according to the invention is generally in the range from 0.1 to 100 mg/kg of body weight of the recipient (mammal) per day and particularly typically in the range from 1 to 10 mg/kg of body weight per day. Thus, the actual amount per day for an adult mammal weighing 70 kg is usually between 70 and 700 mg, where this amount can be administered as an individual dose per day or usually in a series of part-doses (such as, for example, two, three, four, five or six) per day, so that the total daily dose is the same. An effective amount of a salt or solvate or of a physiologically functional derivative thereof can be determined as the fraction of the effective amount of the compound according to the invention per se. It can be assumed that similar doses are suitable for the treatment of other conditions mentioned above.

The invention furthermore relates to medicaments comprising at least one compound according to the invention and/or pharmaceutically usable salts and stereoisomers thereof, including mixtures thereof in all ratios, and at least one further medicament active ingredient.

The invention also relates to a set (kit) consisting of separate packs of (a) an effective amount of a compound according to the invention and/or pharmaceutically usable salts and stereoisomers thereof, including mixtures thereof in all ratios, and
(b) an effective amount of a further medicament active ingredient.

The set comprises suitable containers, such as boxes, individual bottles, bags or ampoules. The set may, for example, comprise separate ampoules, each containing an effective amount of a compound according to the invention and/or pharmaceutically usable derivatives, solvates and stereoisomers thereof, including mixtures thereof in all ratios, and an effective amount of a further medicament active ingredient in dissolved or lyophilised form.

Use

The present compounds are suitable as pharmaceutical active ingredients for mammals, in particular for humans, in the treatment of Diabetes Typ 1 and 2, obesity, neuropathy and/or nephropathy.

The invention thus relates to the use of compounds according to claim 1 and to pharmaceutically usable salts and stereoisomers, including mixtures thereof in all ratios, for the preparation of a medicament for the treatment of Diabetes Type 1 and 2, obesity, neuropathy and/or nephropathy.

The compounds of the present invention can be used as prophylactics or therapeutic agents for treating diseases or disorders mediated by deficient levels of glucokinase activity or which can be treated by activating glucokinase including, but not limited to, diabetes mellitus, impaired glucose tolerance, IFG (impaired fasting glucose) and IFG (impaired fasting glycemia), as well as other diseases and disorders such as those discussed below.

Furthermore, the compounds of the present invention can be also used to prevent the progression of the borderline type, impaired glucose tolerance, IFG (impaired fasting glucose) or IFG (impaired fasting glycemia) to diabetes mellitus.

The compounds of the present invention can be also used as prophylactics or therapeutic agents of diabetic complications such as, but not limited to, neuropathy, nephropathy, retinopathy, cataract, macroangiopathy, osteopenia, diabetic hyperosmolar coma), infectious diseases (e.g., respiratory infection, urinary tract infection, gastrointestinal tract infection, dermal soft tissue infection, lower limb infection etc.), diabetic gangrene, xerostomia, decreased sense of hearing, cerebrovascular disease, peripheral circulatory disturbance, etc.

The compounds of the present invention can be also used as prophylactics or therapeutic agents in the treatment of diseases and disorders such as, but not limited to, obesity, metabolic syndrome (syndrome X), hyperinsulinemia, hyperinsulinemia-induced sensory disorder, dyslipoproteinemia (abnormal lipoproteins in the blood) including diabetic dyslipidemia, hyperlipidemia, hyperlipoproteinemia (excess of lipoproteins in the blood) including type I, II-a (hypercholesterolemia), II-b, III, IV (hypertriglyceridemia) and V (hypertriglyceridemia), low HDL levels, high LDL levels, atherosclerosis and its sequelae, vascular restenosis, neurodegenerative disease, depression, CNS disorders, liver steatosis, osteoporosis, hypertension, renal diseases (e.g., diabetic nephropathy, glomerular nephritis, glomerulosclerosis; nephrotic syndrome, hypertensive nephrosclerosis, terminal renal disorder etc.), myocardiac infarction, angina pectoris, and cerebrovascular disease (e.g., cerebral infarction, cerebral apoplexy).

The compounds of the present invention can be also used as prophylactics or therapeutic agents in the treatment of diseases and disorders such as, but not limited to, osteoporosis, fatty liver, hypertension, insulin resistant syndrome, inflammatory diseases (e.g., chronic rheumatoid arthritis, spondylitis deformans, osteoarthritis, lumbago, gout, postoperative or traumatic inflammation, remission of swelling, neuralgia, pharyngolaryngitis, cystitis, hepatitis (including non-alcoholic steatohepatitis), pneumonia, inflammatory colitis, ulcerative colitis), pancreatitis, visceral obesity syndrome, cachexia (e.g., carcinomatous eachexia, tuberculous cachexia, diabetic cachexia, hemopathic cachexia, endocrinopathic cachexia, infectious cachexia, cachexia induced by acquired immunodeficiency syndrome), polycystic ovary syndrome, muscular dystrophy, tumor (e.g., leukemia, breast cancer, prostate cancer, skin cancer etc.), irritable bowel syndrome, acute or chronic diarrhea, spondylitis deformans, osteoarthritis, remission of swelling, neuralgia, pharyngolaryngitis, cystitis, SIDS, and the like.

The compounds of the present invention can be used in combination with one or more additional drugs such as described below. The dose of the second drug can be appropriately selected based on a clinically employed dose. The proportion of the compound of formula I and the second drug can be appropriately determined according to the administration subject, the administration route, the target disease, the clinical condition, the combination, and other factors. In cases where the administration subject is a human, for instance, the second drug may be used in an amount of 0.01 to 100 parts by weight per part by weight of the compound of formula I.

The second compound of the pharmaceutical combination formulation or dosing regimen preferably has complementary activities to the compound of formula I such that they do not adversely affect each other. Such drugs are suitably present in combination in amounts that are effective for the purpose intended. Accordingly, another aspect of the present invention provides a composition comprising a compound of formula I, or a solvate, metabolite, or pharmaceutically acceptable salt or prodrug thereof, in combination with a second drug, such as described herein.

The compound of formula I and the additional pharmaceutically active agent(s) may be administered together in a unitary pharmaceutical composition or separately and, when administered separately this may occur simultaneously or sequentially in any order. Such sequential administration may be close in time or remote in time. The amounts of the compound of formula I and the second agent(s) and the relative timings of administration will be selected in order to achieve the desired combined therapeutic effect.

The combination therapy may provide "synergy" and prove "synergistic", i.e., the effect achieved when the active ingredients used together is greater than the sum of the effects that results from using the compounds separately. A synergistic effect may be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect may be attained when the compounds are administered or delivered sequentially, e.g., by different injections in separate syringes. In general, during alternation therapy, an effective dosage of each active ingredient is administered sequentially, i.e., serially, whereas in combination therapy, effective dosages of two or more active ingredients are administered together.

The compounds of the present invention can be used, for example in combination with additional drug(s) such as a therapeutic agent for diabetes mellitus, and/or a therapeutic agent for diabetic complications, as defined above.

Examples of known therapeutic agents for diabetes mellitus which can be used in combination with a compound of formula I include insulin preparations (e.g., animal insulin preparations extracted from the bovine or swine pancreas; human insulin preparations synthesized by a genetic engineering technique using *Escherichia coli* or a yeast), a fragment of insulin or derivatives thereof (e.g., INS-i), agents for improving insulin resistance (e.g., pioglitazone hydrochloride, troglitazone, rosiglitazone or its maleate, GI-262570, JTT-50 1, MCC-555, YM-440, KRP-297, CS-Oil, FK-614), alpha-glucosidase inhibitors (e.g., voglibose, acarbose, miglitol, emiglitate), biguanides (e.g., phenformin, metformin, buformin), insulin secretagogues [sulfonylureas (e.g., tolbutamide, glibenclamide, gliclazide, chiorpropamide, tolazamide, acetohexamide, glyclopyramide, glimepiride, glipizide, glybuzole), repaglinide, nateglinide, mitiglinide or its calcium salt hydrate, GLP-1J, dipeptidylpeptidase IV inhibitors (e.g., NVP-DPP-278, PT-100), beta-3 agonists (e.g., CL-3 16243, SR-58611-A, UL-TG-307, SB-226552, AJ-9677, BMS-196085, AZ-40140, etc.), amylin agonists (e.g., pramlintide), phosphotyrosine phosphatase inhibitors (e.g., vanadic acid), gluconeogenesis inhibitors (e.g., glycogen phosphorylase inhibitors, glucose-6-phosphatase inhibitors, glucagon antagonists), SGLT (sodium-glucose cotransporter) inhibitors (e.g., T-1095), and the like. Examples of known therapeutic agents for diabetic complications include aldose reductase inhibitors (e.g., tolrestat, epairestat, zenarestat, zopobestat, minairestat, fidarestat (SNK-860), CT-i 12), neurotrophic factors (e.g., NGF, NT-3, BDNF), neurotrophic factor production secretion promoters, PKC inhibitors (e.g., LY-333531), AGE inhibitors (e.g., ALT946, pimagedine, pyratoxathine, N-phenacylthiazolium bromide (ALT766), EXO-226), active oxygen scavengers (e.g., thioctic acid), and cerebral vasodilators (e.g., tiapuride, mexiletine).

The compounds of the present invention can also be used, for example in combination with antihyperlipidemic agents. Epidemiological evidence has firmly established hyperlipidemia as a primary risk factor in causing cardiovascular disease (CVD) due to atherosclerosis. In recent years, emphasis has been placed on lowering plasma cholesterol levels, and low density lipoprotein cholesterol in particular, as an essential step in prevention of CVD.

Cardiovascular disease is especially prevalent among diabetic subjects, at least in part because of the existence of multiple independent risk factors in this population. Successful treatment of hyperlipidemia in the general population, and in diabetic subjects in particular, is therefore of exceptional medical importance. Examples of antihyperlipidemic agents include statin compounds which are cholesterol synthesis inhibitors (e.g., cerivastatin, pravastatin, simvastatin, lovastatin, atorvastatin, fluvastatin, itavastatin or their salts, etc.), squalene synthase inhibitors or fibrate compounds (e.g., bezafibrate, clofibrate, simfibrate, clinofibrate) having a triglyceride lowering action and the like.

The compounds of the present invention can also be used, for example in combination with hypotensive agents. Hypertension has been associated with elevated blood insulin levels, a condition known as hyperinsulinemia. Insulin, a peptide hormone whose primary actions are to promote glucose utilization, protein synthesis and the formation and storage of neutral lipids, also acts to promote vascular cell growth and increase renal sodium retention, among other things. These latter functions can be accomplished without affecting glucose levels and are known causes of hypertension. Peripheral vasculature growth, for example, can cause constriction of peripheral capillaries, while sodium retention increases blood volume. Thus, the lowering of insulin levels in hyperinsulinemics can prevent abnormal vascular growth and renal sodium retention caused by high insulin levels and thereby alleviates hypertension. Examples of hypotensive agents include angiotensin converting enzyme inhibitors (e.g., captopril, enalapril, delapril), angiotensin II antagonists (e.g., candesartan cilexetil, losartan, eprosartan, valsantan, termisartan, irbesartan, tasosartan), calcium antagonists (e.g., manidipine, nifedipine, nicardipine, amlodipine, efonidipine), and clonidine.

The compounds of the present invention can be used in combination with antiobesity agents. The term "obesity" implies an excess of adipose tissue. Obesity is a well-known risk factor for the development of many very common diseases such as diabetes, atherosclerosis, and hypertension. To some extent appetite is controlled by discrete areas in the hypothalamus: a feeding centre in the ventrolateral nucleus of the hypothalamus (VLH) and a satiety centre in the ventromedial hypothalamus (VMH). The cerebral cortex receives positive signals from the feeding center that stimulate eating, and the satiety center modulates this process by sending inhibitory impulses to the feeding center. Several regulatory processes may influence these hypothalamic centers. The satiety center may be activated by the increases in plasma glucose and/or insulin that follow a meal. Examples of antiobesity agents include antiobesity drugs acting on the central nervous system (e.g., dexfenfluramine, fenfluramine, phentermine, sibutramine, anfepramon, dexamphetamine, mazindol, phenylpropanolamine, clobenzorex), pancreatic lipase inhibitors (e.g. orlistat), beta-3 agonists CL-3 16243, SR-5861 1-A, UL-TG-307, SB-226552, AJ-9677, BMS-196085, AZ-40140), anorectic peptides (e.g., leptin, CNTF (Ciliary Neurotrophic Factor) and cholecystokinin agonists (e.g. lintitript, FPL-1 5849).

Assays
Glucokinase Activation Screening Assay

GK activity (human or rat enzyme) is measured by an coupled enzyme assay using pyruvate kinase (PK) and lactate dehydrogenase (LDH) as coupling enzymes. GK activity is calculated from the decline in NADH monitored photometrically with a microliter plate (MTP) reader at 340 nm. For screening purposes, the GK assay is routinely run in a 384-MTP format, in a total volume of 33 µl/well. 10 µl of the ATP-regeneration solution (in HEPES-buffer*, pH 7.0, 6.73 U/ml pyruvate kinase, 6.8 U/ml lactate dehydrogenase) and 10 µl of the glucokinase-/glucose solution (15 µg/ml, 6.6 mM glucose in HEPES-buffer*, pH 7.0; the concentration of the glucose stock-solution was 660 mM in Millipore $H_2O$) were mixed together with 3 µl of a 10% DMSO solution (in HEPES-buffer*, pH 7.0) containing 3.3-fold the amounts of the compounds to achieve final compound concentrations in the range between 1 nM to 30 µM (sometimes 300 µM) in the assay solution (s. below). The solutions were mixed for 5 sec, and after a centrifugation at 243×g for 5 min, the solutions were preincubated for 25 min at room temperature.

The reaction was started by the addition of 10 µl of the NADH-/ATP-solution (4.29 mM NADH, 4.95 mM ATP, in HEPES-buffer*). The MTP was shaken for 5 sec., and then, the absorbance at 340 nm was monitored continuously in a MTP-reader (TECAN Spectro fluor plus) for the next 27 min (with a MTP-cycling time of 199 sec.). The final concentrations of the various components were as follows: 49.5 mM Hepes, pH 7.0, 1.49 mM PEP, 1.3 mM NADH, 49.5 mM KCl, 4.96 mM $MgCl_2$, 1.5 mM Mg-ATP, 1.98 mM DTT, 2.04 U/ml pyruvate kinase, 2.06 U/milactate-dehydrogenase, 0.91% DMSO, 0.15 µg/well glucokinase, and test compounds in the range between 1 nM and 300 µM.

The change in the optical density ($\Delta OD_{340\ nm}$) in the presence of the compound was expressed relative to the $\Delta OD_{340\ nm,\ ctrl}$ of the control incubation (in the presence of 2 mM glucose and 0.91% DMSO), taking into account the optical density of the blank sample (incubation in the absence of 2 mM glucose). For the determination of the half maximal effective concentration ($EC_{50}$), the %-Ctrl-values were plotted in a semi-logarithmic graph against the conc. of the compound of interest. The data points were fitted to a sigmoid curve function $(f(x)=((\%\text{-}Ctrl_{max}\text{-}\%\text{-}Ctrl_{min})/(1-(EC_{50}/x**^{n(Hill)}))\%\text{-}Ctrl_{min}))$ by a non-linear regression analysis.

Hepes-buffer (50 mM Hepes, pH 7.0, 5 mM $MgCl_2$, 50 mM KCl, 1.5 mM PEP, 0.1% BSA). DTT was added to the Hepes-buffer from a 200× stock solution (in Millipore $H_2O$) freshly each day. The final concentration of DTT in the Hepes-buffer is 2 mM.

Culture of Pancreatic INS-1 Cells

INS-1 cells were cultured in complete medium, RPMI1640 containing 1 mM sodium pyruvate, 50 μM 2-mercaptoethanol, 2 mM glutamine, 10 mM HEPES, 100 IU/mL penicillin, and 100 μg/mL streptomycin (CM), supplemented with 10 mM glucose, and 10% (vol/vol) heat-inactivated fetal calf serum (FCS), as described by Asfari et al. (Endocrinology 130: 167-178, 1992).

Insulin Secretion Assay

INS-1 cells were plated and cultured in 48-well plates. After 2 days of culture, the medium was removed and cells were cultured for 24 h with a medium change to 5 mM glucose, 1% FCS. The cells were then washed with Krebs-Ringer Bicarbonate HEPES buffer (KRBH; 135 mM NaCl; 3.6 mM KCl; 5 mM NaHCO3; 0.5 mM NaH2PO4; 0.5 mM MgCl2; 1.5 mM CaCl2 and 10 mM HEPES; pH 7.4) 0.1% BSA containing 2.8 mM glucose and preincubated for 30 min at 37° C. in the same buffer. The cells were then washed twice and incubated for 1 h in KRBH 0.1% BSA containing 208 or 4.2 mM glucose and different concentrations of the tested molecule. Insulin concentration in the collected supernatants was measured with ELISA using rat insulin antibody (Insulin Rat Elit PLUS, cat. ref 10-1145-01).

In order to illustrate the invention, the following examples are included. However, it is to be understood that these examples do not limit the invention and are only meant to suggest a method of practicing the invention.

Persons skilled in the art will recognize that the chemical reactions described may be readily adapted to prepare a number of other glucokinase activators of the invention, and alternative methods for preparing the compounds of this invention are deemed to be within the scope of this invention. For example, the synthesis of non-exemplified compounds according to the invention may be successfully performed by modifications apparent to those skilled in the art, e.g., by appropriately protecting interfering groups, by utilizing other suitable reagents known in the art other than those described, and/or by making routine modifications of reaction conditions. Alternatively, other reactions disclosed herein or known in the art will be recognized as having applicability for preparing other compounds of the invention.

Above and below, all temperatures are indicated in ° C. In the following examples, "conventional work-up" means: if necessary, water is added, the pH is adjusted, if necessary, to between 2 and 10, depending on the constitution of the end product, the mixture is extracted with ethyl acetate or dichloromethane, the phases are separated, the organic phase is dried over sodium sulfate and evaporated, and the product is purified by chromatography on silica gel and/or by crystallisation. Rf values on silica gel; eluent: ethyl acetate/methanol 9:1.

| Mass spectrometry (MS): | EI (electron impact ionisation) $M^+$ |
| --- | --- |
| | FAB (fast atom bombardment) $(M + H)^+$ |
| | ESI (electrospray ionisation) $(M + H)^+$ |
| | (unless indicated otherwise) |

Melting Points (mp.): melting points are determined with a BÜCHI Melting Point B-540

LC-MS- and HPLC-Conditions

The in the examples mentioned mass data are from LC-MS measurement, the respective ion $(M+H^+$ or $MA-Na^+)$ is given as m/z: Hewlett Packard System of the HP 1100 series with the following characteristics: ionsource: electrospray (positive mode); scan: 100-1000 m/z; fragmentation-voltage: 60 V; gas-temperature: 300° C., DAD: 220 nm.

Flow rate: 2.4 ml/Min. The used splitter reduce the flow rate after the DAD for the MS to 0.75 ml/Min.

Column: Chromolith SpeedROD RP-18e 50-4.6

Solvent: LiChrosolv-quality from the company Merck KGaA

Solvent A: $H_2O$ (0.01% TFA)

Solvent B: ACN (acetonitrile) (0.01% TFA)

Method A: In 2.8 min from 80% A to 100% B, followed by 0.2 min 100% B and 1 min 80% A.

Method B: in 3 min from 95% A to 100% B. Followed by 0.8 min 95% A.

HPLC:

DAD 220 nm

Flow: 3 ml/Min

Column: Chromolith SpeedROD RP-18e 50-4.6

Solvent: LiChrosolv-quality from the company Merck KGaA

Solvent A: $H_2O$ (0.01% TFA)

Solvent B: ACN (0.01% TFA)

Method A: In 2 min from 90% A to 100% B. Followed by 3 min 100% B and 1 min 90% A.

Method B: 1 min 100% A. In 2.5 min from 100% A to 100% B. Followed by 1.5 min 100% B and 1 min 100% A.

The retention time (Rt) from the examples are the measurement results of the LC-MS and/or HPLC.

Preparation of Educts

Preparation of 3-Hydroxy-5-benzyl-benzoic Acid Methyl Ester

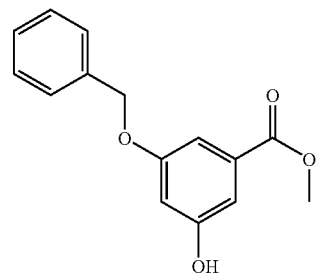

To a solution of methyl 3,5-dihydroxybenzoate (50 g, 297 mmol) in DMF (270 ml) is added under nitrogen $K_2CO_3$ (61.6 g, 446 mmol, 1.5 eq.). Then benzyl bromide (53 ml, 446 mmol, 1.5 eq.) is added dropwise at 0° C. and the reaction mixture is stirred at RT for 24 h. The reaction mixture is filtered over celite, DMF is evaporated, water (500 ml) added and the reaction mixture extracted with ethyl acetate (2×500 ml). The combined organic layer is washed with brine, dried over $MgSO_4$ and the solvent removed in vacuo. The residue is purified by column chromatography (cyclohexane/ethyl acetate 100/00 to 95/05) to give a mixture of the desired product and the di-alkylated compound. This mixture is purified by column chromatography (cyclohexane/acetone 95/05 to 90/10) to give 17.7 g of the title compound as white powder (yield of 23%).

¹H-NMR (CDCl₃, 300 MHz) δ [ppm] 7.28-7.11 (m, 5H), 7.04 (s, 1H), 6.55 (s, 1H), 5.38 (s, 1H), 4.93 (s, 2H), 3.77 (s, 3H).

Preparation of 3-benzyl-5-((S)-2-methoxy-1-methyl-ethoxy)-benzoic Acid Methyl Ester

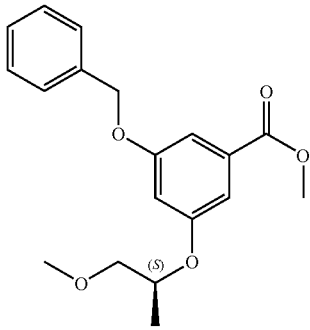

To a solution of previous compound (25 g, 96.8 mmol, 1 eq.) in anhydrous THF (135 ml) is added under inert atmosphere successively triphenyl-phosphine (38.1 g, 145.2 mmol, 1.5 eq.) and (R)-(−)-1-methoxy-2-propanol 98% (10.5 g, 116.2 mmol, 1.2 eq.). The solution is chilled at 0° C. and DIAD (28.8 ml, 145.2 mmol, 1.5 eq.) is added dropwise. Then the reaction mixture is stirred at RT for 16 h, water (200 ml) is added and the residue extracted with ethyl acetate (2×200 ml). The organic phase is dried over MgSO₄ and the solvent removed in vacuo. The residue is purified by column chromatography (cyclohexane/ethyl acetate 10/0 to 9/1) to give 24 g of the title compound as yellow oil (75%, ee=99%).

¹H-NMR (CDCl₃, 300 MHz) δ [ppm] 7.44-7.23 (m, 8H), 6.76 (5, 1H), 5.07 (s, 2H), 4.57 (m, 1H), 3.89 (s, 3H), 3.55 (m, 2H), 3.40 (s, 3H), 1.30 (d, 3H).

Preparation of 3-hydroxy-5-(S)-2-methoxy-1-methyl-ethoxy)-benzoic Acid Methyl Ester

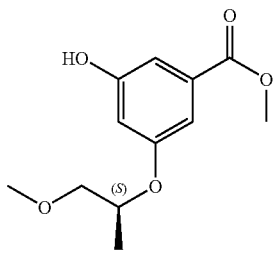

To a solution of previous compound (11 g, 33.3 mmol, 1eq.) in a mixture of THF/MeOH 1/1 (220 ml) is added Pd/C₅% (1.1 g). Then the reaction mixture is hydrogenated at RT for 1 day. The reaction mixture is filtered and concentrated in vacuo to dryness. The residue is purified by column chromatography (cyclohexane/ethyl acetate 7/3) to give 7.5, 94% of the title compound as light yellow oil.

¹H-NMR (CDCl₃, 300 MHz) δ [ppm] 7.13-7.11 (m, 2H), 6.64 (d, 1H), 4.58 (m, 1H), 3.88 (s, 3H), 3.57 (m, 2H), 3.42 (s, 3H), 1.31 (d, 6H).

Preparation of 3-((S)-2-Methoxy-1-methyl-ethoxy)-5-((S)-1-methyl-2-phenyl-ethoxy)-benzoic Acid Methyl Ester

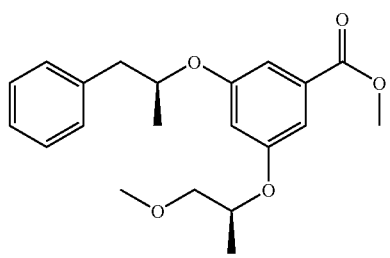

To a solution of previous compound (6.2 g, 25.8 mmol) in THF (190 ml) is added under inert atmosphere successively triphenylphosphine (10.2 g, 38.7 mmol, 1.5 eq.) and (R)-(−)-1-phenyl-2-propanol 97% (4.34 g, 31 mmol, 1.2 eq.). The solution is chilled at 0° C. and DIAD (7.7 ml, 38.7 mmol, 1.5 eq.) is added dropwise. Then the reaction mixture is stirred at RT for 16 h.

The residue is purified by column chromatography (cyclohexane/ethyl acetate 95/05) to give 7.4 g of the title compound as yellow oil (80%, ee>99%).

¹H-NMR (CDCl₃, 300 MHz) δ [ppm] 7.27-7.16 (m, 8H), 6.66 (t, 1H), 4.59 (m, 2H), 3.89 (s, 3H), 3.51 (m, 2H), 3.41 (s, 3H), 3.08 (dd, 1H), 2.82 (dd, 1H), 1.30 (dd, 6H).

Preparation of 3-(S)-2-Methoxy-1-methyl-ethoxy)-5-((S)-1-methyl-2-phenyl-ethoxy)-benzoic Acid

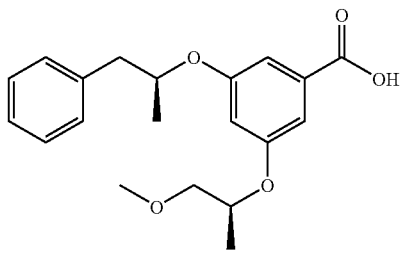

To a solution of previous compound (10.8 g, 30.1 mmol, 1 eq.) in a mixture of THF/MeOH 1/1 (170 ml) is added at 0° C. NaOH 1N (90.4 ml, 90.4 mmol, 3 eq.). Then the reaction mixture is stirred at RT for 16 h and the solvents concentrated in vacuo. The residue is diluted with water (250 ml), the aqueous phase is extracted with ethyl ether (2×125 ml), acidified to pH 3 with conc. HCl and extracted with ethyl acetate. The combined organic layer is dried over MgSO₄ and the solvent removed in vacuo. The residue is purified by column chromatography (diethyl ether/pentane 1/1 to 100/00) to give 9.2 g, 90% of the title compound as light yellow oil;

MS: 345.2 (M+H⁺).

$^1$H-NMR (CDCl$_3$, 300 MHz) δ [ppm] 7.19-7.12 (m, 7H), 6.60 (t, 1H), 4.49 (m, 2H), 3.50-3.378 (two dd, 2H), 3.31 (s, 3H), 2.97 (dd, 1H), 2.72 (dd, 1H), 1.20 (dd, 6H).

EXAMPLE 1

Preparation of 3-Benzyloxy-5-isopropoxy-N-(1-pyridine-2-ylmethyl-1H-pyrazol-3-yl)-benzamide ("A1")

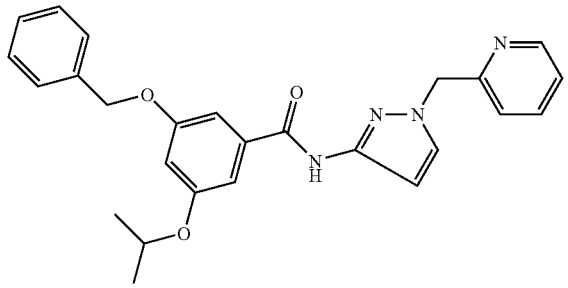

1.1 3,5-Dihydroxy-benzoic acid methyl ester (149 mmol), potassium carbonate (1 eq.) and 18-crown-6 (0.1 eq.) are dissolved in acetone (750 ml) and stirred for 1 hour at RT. Benzylbromide (0.8 eq.) is added and the reaction solution is heated to reflux for 8 hours. The solvent is removed in vacuo and 3-benzyloxy-5-hydroxy-benzoic acid methyl ester is isolated after column chromatography in a yield of 26%. The isolated compound is dissolved in acetone (180 ml), potassium carbonate (1.2 eq.) and isopropyl iodide (2. eq.) is added and the reaction solution is heated under reflux for 24 hours. The reaction is quenched with water and extracted with ethyl acetate. The combined organic layer is dried over Na$_2$SO$_4$ and the solvent removed in vacuo. 3-Benzyloxy-5-isopropoxy-benzoic acid methyl ester is obtained after column chromatography in a yield of 67%. The isolated compound is dissolved in methanol/TNF/water (90 ml, 1:1:1) and LiOH (4 eq.) is added. The reaction is stirred for 2 hours at RT and quenched with citric acid solution and the pH was adjusted to 7. The solution is extracted with ethyl acetate and the combined organic layers are dried over Na$_2$SO$_4$ and the solvent is removed in vacuo. 3-Benzyloxy-5-isopropoxy-benzoic acid is isolated as a brown powder in a yield of 93%; HPLC (Method 8): 3.43 min; LC-MS (Method B): 2.391 min, 287.15 (M+H$^+$);

$^1$H-NMR (DMSO-d$_6$, 500 MHz): δ [ppm] 13.153 (br, 1H), 7.445 (d, 2H, J=7.1 Hz), 7.390 (t, 2H, J=7.1 Hz), 7.324 (t, 1H, J=7.1 Hz), 7.102-7.095 (m, 1H), 7.026-7.019 (m, 1H), 6.713-6.705 (m, 1H), 5.119 (s, 2H), 4.616 (septet, 1H, J=6.1 Hz), 1.253 (d, 6H, J=6.1 Hz).

1.2 3-Amino-pyrazole (278 mmol) is dissolved in acetic acid (240 ml) and isobenzofurane-1,3-dione (1 eq.) is added. The reaction solution is heated to 130° C. for 14 h. After cooling to RT, the precipitate is filtrated and washed with ethylacetate/heptane (1:1). 2-(1H-Pyrazol-3-yl)-isoindole-1,3-dione is obtained as a colourless powder; HPLC (Method B): 2.69 min; LC-MS (Method B): 1.360 min, 214.15 (M+H$^+$).

1.3 2-Chloromethylpyridine hydrochloride (1.0.9 mmol) is dissolved in water and NaOH (32% in water) is added and extracted with dichloromethane. The combined organic layers are dried over MgSO$_4$ and the solvent is removed in vacuo. The remaining residue is added to a suspension of NaH (2 eq.) in DMF at 0° C. Afterwards 2-(1H-Pyrazole-3-yl)-isoindole-1,3-dione (11.7 mmol) is added and the reaction is stirred 15 hours at 50° C. The solvent is removed in vacuo. Hydrazine hydroxide (20 ml) and ethanol (20 ml) is added and the reaction is stirred 3 days at 120° C. The solvent is removed in vacuo and the residue is suspended in dichloromethane and filtrated. The solvent of the filtrate is removed in vacuo. The remaining residue is purified via column chromatography (ethyl acetate/methanol). 1-Pyridine-2-ylmethyl-1H-pyrazole-3-ylamine is isolated as a yellow powder in a yield of 20%; HPLC (Method B): 0.49 min; LC-MS: 0.550 min, 175.15 (M+H$^+$);

$^1$H-NMR (DMSO-d$_6$, 400 MHz): δ [ppm] 8.509-8.493 (m, 1H), 7.754-7.711 (m, 1H), 7.466 (d, 1H, J=2.2 Hz), 7.285-7.251 (m, 1H), 6.943-6.924 (m, 1H), 5.447 (d, 1H, J=2.2 Hz), 5.118 (s, 2H), 4.574 (s, 2H).

1.4 3-Benzyloxy-5-isopropoxy-benzoic acid (0.86 mmol) is dissolved in thionyl chloride (1.6 ml) and heated to 70° C. for one hour. After cooling to RT, the solvent is removed in vacuo. The residue is dissolved in dichloromethane and triethylamine (1.5 eq.) and 1-pyridine-2-ylmethyl-1H-pyrazole-3-ylamine (1.2 eq.) are added. The reaction is stirred 16 hours at RT. 3-Benzyloxy-5-isopropoxy-N-(1-pyridine-2-ylmethyl-1H-pyrazole-3-yl)-benzamide is obtained after column chromatography (heptane/ethyl acetate) as a colorless powder in a yield of 43%; HPLC (Method B): 3.21 min; LC-MS: 2.285 min, 443.15 (M+H$^+$);

$^1$H-NMR (DMSO-d$_6$, 500 MHz): δ [ppm] 10.810 (s, 1H), 8.539-8.524 (m, 1H), 7.827 (d, 1H, J=2.3 Hz), 7.773 (dtf, 1H, J=1.8 Hz, J=7.6 Hz), 7.454-7.440 (m, 2H) 7.408-7.378 (m, 2H), 7.345-7.292 (m, 2H), 7.253-7.246 (m, 1H), 7.169-7.162 (m, 1H), 7.071 (d, 1H, J=7.9 Hz), 6.689-6.673 (m, 2H), 5.366 (s, 2H), 5.138 (s, 2H), 4.681 (septet, 1H, J=6.0 Hz), 1.260 (d, 6H, J=6.0 Hz).

EXAMPLE 2

Preparation of 3-Benzyloxy-5-isopropoxy-N-(5-methyl-1-pyridine-2-ylmethyl-1H-pyrazole-3-yl)-benzamide ("A2")

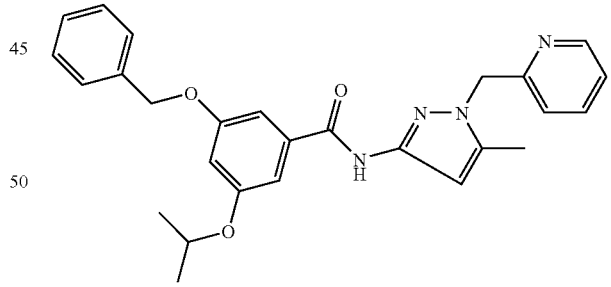

3-Benzyloxy-5-isopropoxy-benzoic acid (0.35 mmol) is dissolved in acetonitrile, di-isopropyl ethyl amine (3 eq.), benzotriazole-1-yl-oxy-tris-(dimethylamino)-phosphonium (1.2 eq.) and 5-methyl-1-pyridine-2-ylmethyl-1H-pyrazole-3-ylamine (1.0 eq., prepared similar to 1-pyridine-2-ylmethyl-1H-pyrazole-3-ylamine) is added and stirred at RT for 14 hours. The solvent is removed in vacuo. 3-Benzyloxy-5-isopropoxy-N-(5-methyl-1-pyridine-2-ylmethyl-1H-pyrazole-3-yl)-benzamide is obtained after column chromatography (chloroform (methanol) as a colourless powder in a yield of 31%; HPLC (Method B): 3.25 min; LC-MS: 2.350 min, 457.15 (M+H$^+$);

$^1$H-NMR (DMSO-d$_6$, 500 MHz): δ [ppm] 10.708 (s, 1H), 8.529 (d, 1H, J=4.3 Hz), 7.766 (dt, 1H, J=1.8 Hz, J=7.7 Hz), 7.449 (d, 2H, J=7.3 Hz), 7.394 (t, 2H, J=7.3 Hz), 7.342-7.285 (m, 2H), 7.246 (s, 1H), 7.161 (s, 1H), 6.980 (d, 1H, J=7.9 Hz), 6.674 (t, 1H, J=2.2 Hz), 6.527 (s, 1H), 5.301 (s, 2H), 5.139 (s, 2H), 4.683 (septett, 1H, J=6.0 Hz), 2.293 (s, 3H), 1.259 (d, 6H, J=6.0 Hz).

EXAMPLE 3

Preparation of 3-Benzyloxy-N-(1-benzyl-1H-pyrazol-3-yl)-5-isopropoxy-benzamide ("A3")

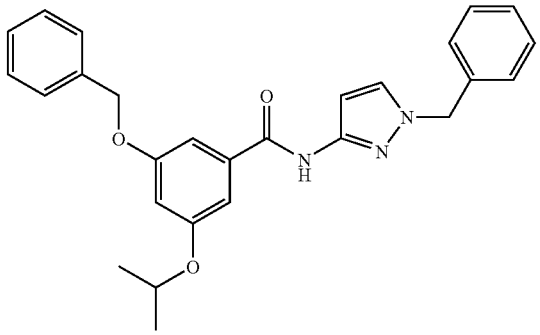

3.1 2-(1H-Pyrazole-3-yl)-isoindole-1,3-dione (11.7 mmol) is added to a suspension of NaH (2 eq.) in DMF at 0° C. Benzylbromide (1 eq.) is added and the reaction is stirred 15 h at 50° C. The solvent is removed in vacuo. Hydrazine hydroxide (10 ml) and ethanol (20 ml) are added and the reaction is stirred 17 hours at 120° C. The precipitate is filtered and the solvent is removed in vacuo. The residue is suspended in dichloromethane and filtrated. The solvent of the filtrate is removed in vacuo. The remaining residue is purified via column chromatography (Ethyl acetate/methanol). 1-Benzyl-1H-pyrazole-3-ylamine is isolated as a yellow powder in a yield of 32%; HPLC (Method B): 2.45 min; LC-MS (Method B): 1.203 min, 174.15 (M+H$^+$);

$^1$H-NMR (DMSO-d$_6$, 400 MHz): δ [ppm] 7.432 (d, 1H, J=2.2 Hz)), 7.344-7.300 (m, 2H), 7.282-7.239 (m, 1H), 7.195-7.174 (m, 2H), 5.421 (d, 1H, J=2.2 Hz), 5.028 (s, 2H), 4.548 (s, 2H).

3.2 Triphenylphosphin (0.59 mmol) is dissolved in dichloromethane (0.8 ml) and N-bromo-succinimide (0.59 mmol) is added at 0° C. After 30 min 3-benzyloxy-5-isopropoxy-benzoic acid (0.35 mmol) in dichloromethane (1.2 ml) is added. After 45 min, the reaction solution is allowed to warm to RT. 1-Benzyl-1H-pyrazole-3-ylamine (0.44 mmol) is added to the reaction solution and stirred 8 hours at RT.

Triphenylphosphin (1 mmol) and N-bromo-succinimide (0.6 mmol) is added and the reaction is stirred 20 hours at RT. The solvent is removed in vacuo and the residue dissolved in ethyl acetate and extracted with saturated sodium carbonate solution and brine. The organic layer is dried over MgSO$_4$ and the solvent is removed in vacuo. 3-Benzyloxy-N-(1-benzyl-1H-pyrazole-3-yl)-5-isopropoxy-benzamide is isolated after column chromatography (heptane I ethyl acetate) as a yellow powder in a yield of 25%; HPLC (Method B): 3.65 min; LC-MS (Method B): 2.720 min, 442.15 (M+H$^+$);

$^1$H-NMR (DMSO-d$_5$, 500 MHz): δ [ppm] 10.793 (s, 1H), 7.795 (d, 1H, J=2.3 Hz), 7.458-7.441 (m, 2H), 7.409-7.395 (m, 2H), 7.364-7.271 (m, 4H), 7.250-7.233 (m, 3H), 7.168-7.161 (m, 1H), 6.681-6.672 (m, 1H), 6.654 (d, 1H, J=2.3 Hz), 5.262 (s, 2H), 5.140 (s, 2H), 4.683 (septett, 1H, J=6.1 Hz), 1.261 (d, 6H, J=6.1 Hz).

EXAMPLE 4

Preparation of N-(1-benzyl-1H-pyrazole-3-yl)-3-(S)-2-methoxy-1-methyl-ethoxy)-5-(S)-1-methyl-2-phenyl-ethoxy)-benzamide ("A4")

"A4"

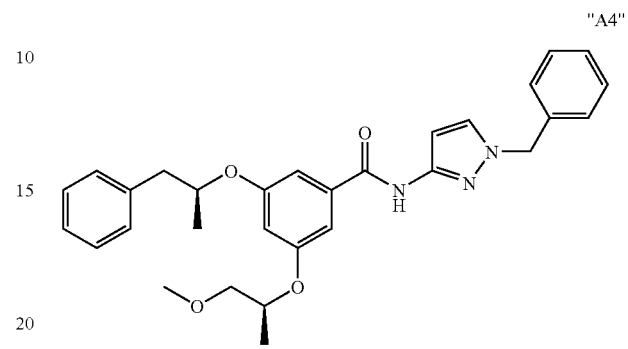

Triphenylphosphin (0.5 mmol) is dissolved in dichloromethane (0.6 ml) and N-bromosuccinimide (0.0.5 mmol) is added at 0° C. After 30 min 3-((S)-2-Methoxy-1-methyl-ethoxy)-5-((S)-1-methyl-2-phenyl-ethoxy)-benzoic acid (0.29 mmol) in dichloromethane (0.6 ml) is added. After 30 min, the reaction solution is allowed to warm to RT. 1-Benzyl-1H-pyrazole-3-ylamine (0.38 mmol) is added to the reaction solution and stirred 8 hours at RT. Triphenylphosphin (0.5 mmol) and N-bromosuccinimide (0.0.5 mmol) is added and the reaction is stirred 20 hours at RT. The solvent is removed in vacuo and the residue dissolved in ethyl acetate and extracted with saturated sodium carbonate solution and brine. The organic layer is dried over MgSO$_4$ and the solvent is removed in vacuo. "A4" is isolated after column chromatography (Heptan/Ethyl acetate) as an colorless oil in a yield of 33%; HPLC (Method B): 3.67 min; LC-MS (Method 8): 2.724 min, 500.2 (MH$^+$);

$^1$H-NMR (DMSO-d$_6$, 500 MHz): δ [ppm] 10.7780 (s, 1H), 7.792 (d, 1H, J=2.3 Hz), 7.363-7.332 (m, 2H), 7.303-7.269 (m, 5H), 7.248-7.231 (m, 2H), 7.211-7.176 (m, 1H), 7.141-7.137 (m, 2H), 6.648 (d, 1H, J=2.3 Hz), 6.579 (t, 1H, J=2.3 Hz), 5.269 (s, 2H), 4.794-4.746 (m, 1H), 4.696-4.640 (m 1H), 3.483 (dd, 1H, J=5.9 Hz, J=10.6 Hz), 3.429 (dd, 1H, J=4.2 Hz, J=10.6 Hz), 3.316 (s, 3H), 2.974 (dd, 1H, J=6.4 Hz, J=13.8 Hz), 2.857 (dd, 1H, J=5.8 Hz, J=13.8 Hz), 1.229-1.202 (m, 6H).

EXAMPLE 5

Preparation of 3-((S)-2-Methoxy-1-methyl-ethoxy)-5-((S)-1-methyl-2-phenyl-ethoxy)-N-(1-pyridine-2-ylmethyl-1H-pyrazole-3-yl)-benzamide ("A5")

"A5"

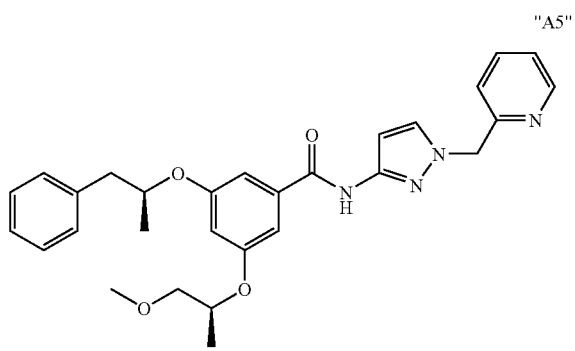

3-((S)-2-Methoxy-1-methyl-ethoxy)-5-((S)-1-methyl-2-phenyl-ethoxy)-benzoic acid (058 mmol) is dissolved in thionylchloride (1.1 ml) and heated to 70° C. for 1 hour. After cooling to RT, the solvent is removed in vacuo. The residue is dissolved in dichloromethane (1.2 ml) and ethyldiisopropylamin (150 μl) is added and 1-pyridine-2-ylmethyl-1H-pyrazole-3-ylamine (0.70 mmol) is added. The suspension is stirred 21 hours at room temperature. The reaction solution is extracted with water. The organic layer is washed with brine and dried over MgSO$_4$ and the solvent is removed in vacuo. "A5" is isolated after reversed phase column chromatography (water/acetonitrile) as yellow oil in a yield of 34%; HPLC (Method B): 3.24 min; LC-MS (Method B): 2316 min, 501.2 (MH$^+$);

$^1$H-NMR (DMSO-d$_6$, 500 MHz): δ [ppm] 10.800 (s, 1H), 8.540-8.525 (m, 1H), 7.826 (d, 1H, J=2.3 Hz), 2.974 (dt, 1H, J=1.9 Hz, J=7.6 Hz), 7.321-7.276 (m, 5H), 7.210-7.176 (m, 1H), 7.143-7.139 (m, 2H), 7.080-7.064 (m, 1H), 6.681 (d, 1H, J=2.3 Hz), 6.582 (t, 1H, J=2.3 Hz), 5.365 (s, 2H), 4.782-4.745 (m, 1H), 4.684-4.650 (m, 1H), 3.481 (dd, 1H, J=5.9 Hz, J=13.8 Hz), 3.428 (dd, 1H, J=4.1 Hz, J=13.8 Hz), 3.304 (s, 3H), 2.972 (dd, 1H, J=6.5 Hz, J=13.8 Hz), 2.855 (dd, 1H, J=5.9 Hz, J=13.8 Hz), 1.228-1.201 (m, 6H).

EXAMPLE 6

Preparation of 3-isopropoxy-N-(1-pyridine-2-ylmethyl-1H-pyrazole-3-yl)-5-(2-thiophene-3-yl-ethoxy)-benzamide ("A6")

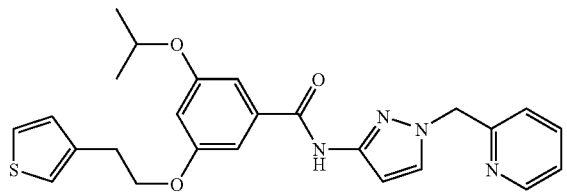

Step A: To a solution of 3-hydroxy-5-isopropoxy-benzoic acid methyl ester (71.4 mmol) in anhydrous THF (85 ml) is added under inert atmosphere successively triphenylphosphine (1.5 eq.) and 2-(3-thienyl)ethanol (1.3 eq.). The solution is chilled at 0° C. and DIAD [diisopropylazodicarboxylate] (21.65 g, 107.1 mmol, 1.5 eq.) is added dropwise. Then the reaction mixture is stirred at room temperature for 20 h and concentrated in vacuo. 3-Isopropoxy-5-(2-thiophene-3-yl-ethoxy)-benzoic acid methyl ester is obtained after column chromatography (cyclohexane/ethyl acetate) as yellow oil in a yield of 41%.

$^1$H-NMR (CDCl$_3$, 300 MHz) δ [ppm] 7.25 (s, 1H), 7.14 (d, 2H), 7.06 (d, 1H), 7.02 (d, 1H), 6.61 (s, 1H), 4.55 (m, 1H), 4.16 (t, 2H), 3.86 (s, 3H), 3.10 (t, 2H), 1.30 (m, 6H).

Step B: To a solution of 3-isopropoxy-5-(2-thiophene-3-yl-ethoxy)-benzoic acid methyl ester (9.5 mmol) in a mixture of THF/MeOH 1/1 (40 ml) is added at 0° C. NaOH 1N (28.6 ml). Then the reaction mixture is stirred at room temperature for 6 h and the solvents are concentrated in vacuo. The residue is diluted with water (100 ml), the aqueous phase is extracted with ethyl ether (2×50 ml), acidified to pH 3 with conc. HCl and extracted with ethyl acetate (2×100 ml). The combined organic layer is washed with brine (50 ml), dried over MgSO$_4$ and the solvent removed in vacuo. The residue is triturated with ethyl ether and pentane then filtered. 3-Isopropoxy-5-(2-thiophene-3-yl-ethoxy)-benzoic acid is obtained as white powder in a yield of 90%; MS: 307.1 (M+H$^+$);

$^1$H-NMR (CDCl$_3$, 300 MHz) δ [ppm] 7.30-7.22 (m, 3H), 7.10 (d, 1H), 7.04 (d, 1H), 6.68 (s, 1H), 4.59 (m, 1H), 4.21 (t, 2H), 3.14 (t, 2H), 1.35 (m, 6H).

Step C: 3-Isopropoxy-5-(2-thiophene-3-yl-ethoxy)-benzoic acid (0.24 mmol) is dissolved in thionylchloride (0.5 ml) and heated to 70° C. for 1 hour. After cooling to RT, the solvent is removed in vacuo. The residue is dissolved in dichloromethane (1.2 ml) and ethyldiisopropylamine (73 μl) is added and 1-pyridine-2-ylmethyl-1H-pyrazole-3-ylamine (1 eq.) is added. The suspension is stirred 14 hours at room temperature. The reaction solution is extracted with water. The organic layer is washed with brine and dried over MgSO$_4$ and the solvent is removed in vacuo. 3-Isopropoxy-N-(1-pyridine-2-ylmethyl-1H-pyrazole-3-yl)-5-(2-thiophene-3-yl-ethoxy)-benzamide. ("A6") is isolated after column chromatography (heptane/ethyl acetate) as colorless oil in a yield of 51%; HPLC (method B): 3.23 min; LC-MS (method B): 1.97 min, 463.2 (M+H$^+$);

$^1$H-NMR (DMSO-d$_6$, 500 MHz): δ [ppm] 10.807 (s, 1H), 8.545-8.530 (m, 1H), 7.832 (d, 1H, J=2.3 Hz), 7.782 (df, 1H, J=1.8 Hz, J=7.6 Hz), 7.476 (dd, 1H, J=2.9 Hz, J=4.9 Hz), 7.327-7.304 (m, 2H), 7.178-7.147 (m, 2H), 7.118 (dd, 1H, J=1.2 Hz, J=4.9 Hz), 7.080 (d, 1H, J=7.8 Hz), 6.688 (d, 1H, J=2.1 Hz), 6.620 (t, 1H, J=2.1 Hz), 5.368 (s, 2H), 4.709-4.658 (m, 1H), 4.231 (t, 2H, J=6.6), 3.057 (t, 2H, J=6.6 Hz), 1.270 (d, 6H, J=6.0 Hz).

EXAMPLE 7

Preparation of 3-((S)-2-methoxy-1-methyl-ethoxy)-5-((S)-1-methyl-2-phenyl-ethoxy)-N-(1-pyridine-3-ylmethyl-1H-pyrazole-3-yl)-benzamide ("A7")

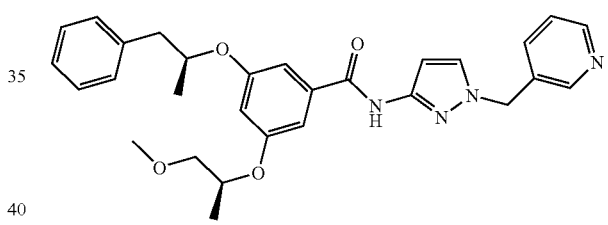

Step A: NaH (0.9 g., 60% suspension in liquid paraffin) is dissolved in DMF (10 ml) and 2-(1H-pyrazole-3-yl)-isoindole-1,3-dione (11.7 mmol) is added at 0° C. To this solution is added 3-chloromethyl-pyridine (10.1 mmol) and the mixture is heated to 50° C. for 16 hours. The solvent is removed in vacuo. The residue is dissolved in ethanol (100 ml) and hydrazinium-hydroxide (30 ml) is added and the reaction is heated to 120° C. for 9 days. The solvent is removed in vacuo. 1-Pyridine-3-ylmethyl-1H-pyrazole-3-ylamine is obtained after column chromatography as colorless oil in a yield of 62%; LC-MS (method B): 0.39 min, 175.15 (M+H$^+$).

Step B: 3-(S)-2-Methoxy-1-methyl-ethoxy)-5-((S)-1-methyl-2-phenyl-ethoxy)-benzoic acid (0.58 mmol) is dissolved in thionylchloride (1.1 ml) and heated to 70° C. for 1 hour. After cooling to room temperature, the solvent is removed in vacuo. The residue is dissolved in dichloromethane (1.2 ml) and ethyldiisopropylamine (150 up is added and 1-pyridine-3-ylmethyl-1H-pyrazole-3-ylamine (1 eq.) is added. The suspension is stirred 17 hours at room temperature. The reaction solution is extracted with water. The organic layer is washed with water and brine and dried over MgSO$_4$ and the solvent is removed in vacuo. 3-((S)-2-Methoxy-1-methyl-ethoxy)-5-((S)-1-methyl-2-phenyl-ethoxy)-N-(1-pyridine-3-ylmethyl-1H-pyrazole-3-yl)-benzamide ("A7") is isolated after column chromatography as colorless oil in a yield of 13%; HPLC (method B): 3.19 min; LC-MS (method B): 2.08 min, 501.2 (M+H$^+$);

$^1$H-NMR (DMSO-$d_6$, 500 MHz): δ [ppm] 10.782 (s, 1H), 8.520-8.500 (m, 2H), 7.843 (d, 1H, J=2.3 Hz), 7.646-7.623 (m, 1H), 7.393-7.366 (m, 1H), 7.286-7.276 (m, 4H), 7.211-7.176 (m, 1H), 7.133 (d, 2H, J=2.2 Hz), 6.659 (d, 1H, J=2.3 Hz), 6.581 (t, 1H, J=2.2 Hz), 5.316 (s, 2H), 4.780-4.743 (m, 1H), 4.683-4.650 (m, 1H), 3.482 (dd, 1H, J=5.9 Hz, J=10.4 Hz), 3.429 (dd, 1H, J=4.1 Hz, J=10.4 Hz), 3.284 (s, 3H), 2.972 (dd, 1H, J=6.5 Hz, J=13.7 Hz), 2.856 (dd, 1H, J=5.8 Hz, J=13.8 Hz), 1.228-1.201 (m, 6H).

EXAMPLE 8

Preparation of 3-((S)-2-methoxy-1-methyl-ethoxy)-5-((S)-1-methyl-2-phenyl-ethoxy)-N-(1-pyridine-4-ylmethyl-1H-pyrazole-3-yl)-benzamide ("A8")

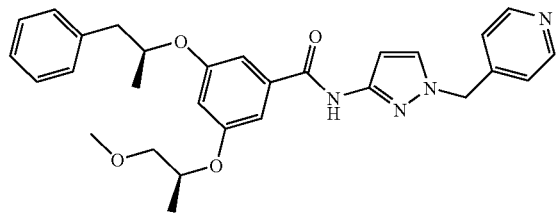

Step A: NaH (0.9 g., 60% suspension in liquid paraffin) is dissolved in DMF (10 ml) and 2-(1H-pyrazole-3-yl)-isoindole-1,3-dione (11.7 mmol) is added at 0° C. To this solution is added 4-chloromethyl-pyridine (11.7 mmol) and the mixture is heated to 50° C. for 16 hours. The solvent is removed in vacuo. The residue is dissolved in ethanol (100 ml) and hydrazinium-hydroxide (70 ml) is added and the mixture is heated to 120° C. for 9 days. The solvent is removed in vacuo. 1-Pyridine-4-ylmethyl-1H-pyrazole-3-ylamine is obtained after column chromatography as colorless oil in a yield of 83%; LC-MS (method B): 0.44 min, 175.15 (M+H$^+$);

Step B: 3-((S)-2-Methoxy-1-methyl-ethoxy)-5-((S)-1-methyl-2-phenyl-ethoxy)-benzoic acid (0.58 mmol) is dissolved in thionylchloride (1.1 ml) and heated to 70° C. for 1 hour. After cooling to RT, the solvent is removed in vacuo. The residue is dissolved in dichloromethane (1.2 ml) and ethyldiisopropylamine (150 μl) is added and 1-pyridine-4-ylmethyl-1H-pyrazole-3-ylamine (1.2 eq.) is added. The suspension is stirred 4 days at room temperature. The reaction solution is extracted with water. The organic layer is washed with water and brine and dried over MgSO$_4$ and the solvent is removed in vacuo. 3-(S)-2-Methoxy-1-methyl-ethoxy)-5-(S)-1-methyl-2-phenyl-ethoxy)-N-(1-pyridine-4-ylmethyl-1H-pyrazole-3-yl)-benzamide ("A8") is isolated after column chromatography as colorless oil in a yield of 17%; HPLC (method B): 3.17 min; LC-MS (method B): 1.98 min, 501.3 (M+H$^+$);

$^1$H-NMR (DMSO-$d_6$, 500 MHz): δ [ppm] 10.811 (s, 1H), 8.535-8.523 (m, 2H), 7.849 (d, 1H, J=2.4 Hz), 7.286-7.277 (m, 4H), 7.211-7.183 (m, 1H), 7.150-7.139 (m, 4H), 6.700 (d, 1H, J=2.3 Hz), 6.586 (t, 1H, J=2.2 Hz), 5.337 (s, 2H), 4.782-4.746 (m, 1H), 4.685-4.652 (m, 1H), 3.483 (dd, 1H, J=5.9 Hz, J=10.6 Hz), 3.430 (dd, 1H, J=4.1 Hz, J=10.6 Hz), 3.263 (s, 3H), 2.974 (dd, 1H, J=6.5 Hz, J=13.7 Hz), 2.858 (dd, 1H, J=5.8 Hz, J=13.7 Hz), 1.230-1.202 (m, 6H).

EXAMPLE 9

Preparation of N-(1-Benzyl-1H-pyrazol-3-yl)-3-isopropoxy-5-(2-thiophen-3-yl-ethoxy)-benzamide ("A9")

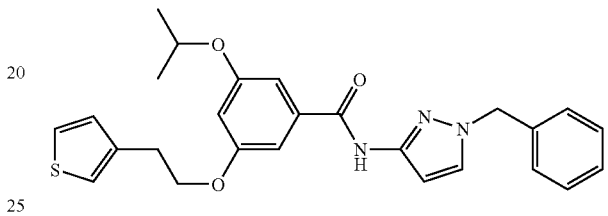

3-Isopropoxy-5-(2-thiophen-3-yl-ethoxy)-benzoic acid (0.672 mmol) is dissolved in thionylchloride (1.2 ml) and heated to 70° C. for 1 hour. After cooling to room temperature, the solvent is removed in vacuo. The residue is dissolved in dichloromethane (1.2 ml) and ethyldiisopropyl-amine (167 μl) is added and 1-benzyl-1H-pyrazol-3-ylamine (1.2 eq) is added. The solution is stirred 21 hours at room temperature. The reaction solution is extracted with water. The organic layer is washed with brine and dried over MgSO4 and the solvent is removed in vacuo. N-(1-Benzyl-1H-pyrazol-3-yl)-3-isopropoxy-5-(2-thiophen-3-yl-ethoxy)-benzamide is isolated after column chromatography (heptan /ethylacetate) as yellow oil in a yield of 45%; HPLC (method B): 3.63 min; LC-MS (method B): 2.74 min, 462.2 (MH$^+$); $^1$H-NMR (DMSO-$d_5$, 500 MHz): δ [ppm] 10.78 (s, 1), 7.79 (d, 1H, J=2.2 Hz), 7.468 (dd, 1H, J=3 Hz, J=4.9 Hz), 7.359-7.269 (m, 4H), 7.245-7.228 (m, 2H), 7.174-7.139 (m, 2H), 7.11 (dd, 1H, J=1.1 Hz, J=4.9 Hz), 6.648 (d, 1H, J=2.2 Hz), 5.256 (s, 2H), 4.678 (sep, 1H, J=6 Hz), 4.223 (t, 2H, J=6.9 Hz), 3.049 (t, 2H, J=6.9 Hz), 1.262 (d, 6H, J=6 Hz).

EXAMPLE 10

Preparation of 3-(4-methanesulfonyl-phenoxy)-5-(S)-2-methoxy-1-methyl-ethoxy)-N-(1-pyridin-3-ylmethyl-1H-pyrazol-3-yl)-benzamide ("A10")

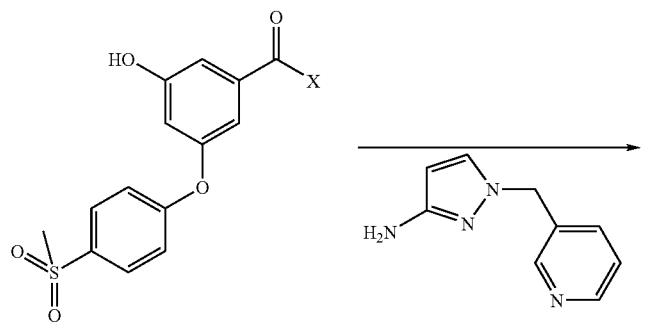

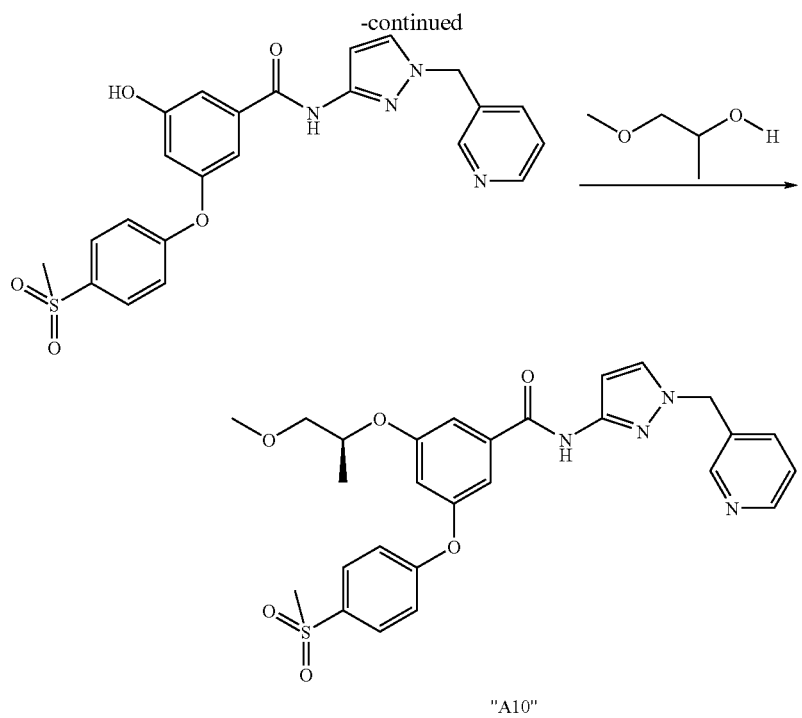

X = OH, Cl, Br, activated OH $^1$H-NMR (DMSO-d$_6$, 500 MHz): δ [ppm] 10.895 (S, 1H), 8.509-8.490 (m, 2H), 7.938-7.920 (m, 2H), 7.841 (d, 1H, J=2.3 Hz), 7.634-7.618 (m, 1H), 7.482-7.476 (m, 1H), 7.371 (dd, 1H, J=4.8 Hz, J=7.8 Hz), 7.285 (sb, 1H), 7.235-7.217 (m, 2H), 6.904 (t, 1H, J=2.2 Hz), 6.645 (d, 1H, J=2.3 Hz), 5.308 (s, 2H), 4.775-4.727 (m, 1H), 3.522-3.447 (m, 2H), 3.286 (s, 3H), 3.196 (s, 3H), 1.236 (d, 3H, J=6.3 Hz).

Pharmacological Data

TABLE 1

Glucokinase Activation Assay

| compound nr. | fold activation (human) | EC$_{50}$ (human) |
|---|---|---|
| "A1" | D | B |
| "A2" | C | B |
| "A3" | C | A |
| "A4" | E | A |
| "A5" | E | A |
| "A6" | E | A |
| "A7" | E | A |
| "A8" | E | A |
| "A9" | D | A |
| "A10" | E | A |

EC$_{50}$:
10 nM-1 μM = A
1 μM-10 μM = B
fold activation:
1.2 μM-5 μM = C
5 μM-10 μM = D
>10 μM = E The Following Examples Relate to Pharmaceutical Preparations:

EXAMPLE A

Injection Vials

A solution of 100 g of an active ingredient according to the invention and 5 g of disodium hydrogenphosphate in 3 l of bidistilled water is adjusted to pH 6.5 using 2N hydrochloric acid, sterile filtered, transferred into injection vials, lyophilised under sterile conditions and sealed under sterile conditions. Each injection vial contains 5 mg of active ingredient.

EXAMPLE B

Suppositories

A mixture of 20 g of an active ingredient according to the invention with 100 g of soya lecithin and 1400 g of cocoa butter is melted, poured into moulds and allowed to cool. Each suppository contains 20 mg of active ingredient.

EXAMPLE C

Solution

A solution is prepared from 1 g of an active ingredient according to the invention, 9.38 g of NaH$_2$PO$_4$.2H$_2$O, 28.48 g of Na$_2$HPO$_4$ 1.2H$_2$O and 0.1 g of benzalkonium chloride in 940 ml of bidistilled water. The pH is adjusted to 6.8, and the solution is made up to 1 l and sterilised by irradiation. This solution can be used in the form of eye drops.

EXAMPLE D

Ointment 500 mg of an active ingredient according to the invention are mixed with 99.5 g of Vaseline under aseptic conditions.

EXAMPLE E

Tablets

A mixture of 1 kg of active ingredient according to the invention, 4 kg of lactose, 1.2 kg of potato starch, 0.2 kg of talc and 0.1 kg of magnesium stearate is pressed to give tablets in a conventional manner in such a way that each tablet contains 10 mg of active ingredient.

EXAMPLE F

Dragees

Tablets are pressed analogously to Example E and subsequently coated in a conventional manner with a coating of sucrose, potato starch, talc, tragacanth and dye.

EXAMPLE G

Capsules 2 kg of active ingredient according to the invention are introduced into hard gelatine capsules in a conventional manner in such a way that each capsule contains 20 mg of the active ingredient.

EXAMPLE H

Ampoules

A solution of 1 kg of an active ingredient according to the invention in 60 l of bidistilled water is sterile filtered, transferred into ampoules, lyophilised under sterile conditions and sealed under sterile conditions. Each ampoule contains 10 mg of active ingredient.

The invention claimed is:
1. A compound of formula I

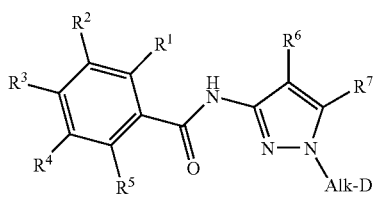

I in which

| | |
|---|---|
| $R^1$, $R^2$, $R^3$, $R^4$, $R^5$ | each, independently of one another, denote H, A, OA, Hal, $[C(R^{12})_2]_m Ar$, $[C(R^{12})_2]_m Het$, $[C(R^{12})_2]_m O[C(R^{12})_2]_m R^{12}$, $S(O)_n R^{12}$, $NR^{10}R^{11}$, $NO_2$, CN, $COOR^{10}$, $CONR^{10}R^{11}$, $NR^{10}COR^{11}$, $NR^{10}CONR^{10}R^{11}$, $NR^{10}SO_n R^{11}$, $COR^{10}$, $SO_3H$, $SO_n NR^{10}R^{11}$, O-Alk-$NR^{10}R^{11}$, $O[C(R^{12})_2]_m CONR^{10}R^{11}$, O-Alk-$NR^{10}COR^{11}$, $O[C(R^{12})_2]_m Het$, $O[C(R^{12})_2]_m Ar$, $S(O)_n[C(R^{12})_2]_m Het$ or $S(O)_n[C(R^{12})_2]_m Ar$, |
| $R^6$, $R^7$ | each, independently of one another, denote H, A, $[C(R^{12})_2]_m Ar$, $[C(R^{12})_2]_m Het$, $[C(R^{12})_2]_m OCOA$, $[C(R^{12})_2]_m O[C(R^{12})_2]_m R^{12}$, $S(O)_n R^{12}$, $NR^{10}R^{11}$, CN, $COOR^{10}$, $CONR^{10}R^{11}$, $NR^{10}COR^{11}$, $NR^{10}CONR^{10}R^{11}$, $NR^{10}SO_n R^{11}$, $COR^{10}$, $SO_3H$, $SO_n NR^{10}R^{11}$, O-Alk-$NR^{10}R^{11}$, $O[C(R^{12})_2]_m CONR^{10}R^{11}$, O-Alk-$NR^{10}COR^{11}$, $O[C(R^{12})_2]_m Het$, $O[C(R^{12})_2]_m Ar$, $S(O)_n[C(R^{12})_2]_m Het$ or $S(O)_n[C(R^{12})_2]_m Ar$, |
| D | denotes Ar or Het, |
| $R^{10}$, $R^{11}$ | each, independently of one another, denote H, A, Ar or Het, |
| A | denotes unbranched or branched alkyl having 1-10 C atoms, in which one or two non-adjacent $CH_2$ groups may be replaced by O, S, SO, $SO_2$, NH, NA', NAr, NHet and/or by —CH=CH— groups and/or in addition 1-7 H atoms may be replaced by OH, F, Cl, Br, =S, =$NR^{12}$ and/or =O or denotes cycloalkyl having 3-7 C atoms, which is unsubstituted or mono-, di- or trisubstituted by =O, F, Cl, OH, OA', OAr', OHet', $SO_n A'$, $SO_n Ar'$, $SO_n Het'$, $NH_2$, NHA', NA'$_2$, NHAr' and/or NHHet', |
| A' | denotes unbranched or branched alkyl having 1-6 C atoms in which 1-7 H atoms may be replaced by F and/or Cl, |
| Alk | denotes unbranched or branched alkylene having 1, 2, 3 or 4 C atoms, |
| Ar | denotes phenyl, naphthyl or biphenyl, each of which is unsubstituted or mono-, di-, tri-, tetra- or pentasubstituted by A, Hal, $[C(R^{12})_2]_m Ar'$, $[C(R^{12})_2]_m Het'$, $O[C(R^{12})_2]_m R^{12}$, $S(O)_n R^{12}$, $NH_2$, NHA', NA'$_2$, NHAr', NHHet', $NO_2$, CN, $COOR^{12}$, $CON(R^{12})_2$, $NR^{12}COR^{12}$, $NR^{12}CON(R^{12})_2$, $NR^{12}SO_n R^{12}$, $COR^{12}$, $SO_3H$, $SO_n N(R^{12})_2$, O-Alk-$N(R^{12})_2$, $O[C(R^{12})_2]_m CON(R^{12})_2$, O-Alk-$NR^{12}COR^{12}$, $O[C(R^{12})_2]_m Het'$, $O[C(R^{12})_2]_m Ar'$, $S(O)_n[C(R^{12})_2]_m Het'$ and/or $S(O)_n[C(R^{12})_2]_m Ar'$, |
| Het | denotes a mono- or bicyclic saturated, unsaturated or aromatic heterocycle having 1 to 4 N, O and/or S atoms, which may be mono-, di- or trisubstituted by Hal, A, $[C(R^{12})_2]_m Ar'$, $[C(R^{12})_2]_m Het'$, $O[C(R^{12})_2]_m Ar'$, $O[C(R^{12})_2]_m Het'$, $[C(R^{12})_2]_m$cycloalkyl, $[C(R^{12})_2]_m OR^{12}$, $[C(R^{12})_2]_m N(R^{12})_2$, $NO_2$, CN, $[C(R^{12})_2]_m COOR^{12}$, $O[C(R^{12})_2]_m COOR^{12}$, $[C(R^{12})_2]_m CON(R^{12})_2$, $[C(R^{12})_2]_m CONR^{12}N(R^{12})_2$, $O[C(R^{12})_2]_m CON(R^{12})_2$, $O[C(R^{12})_2]_m CONR^{12}N(R^{12})_2$, $[C(R^{12})_2]_m NR^{12}COA$, $NR^{12}CON(R^{12})_2$, $[C(R^{12})_2]_m NR^{12}SO_2 A$, $COR^{12}$, $SO_2 N(R^{12})_2$, $S(O)_m A$, =S, =$NR^2$ and/or =O (carbonyl oxygen), |
| Ar' | denotes phenyl, naphthyl or biphenyl, each of which is unsubstituted or mono-, di- or trisubstituted by Hal, A, $OR^{12}$, $N(R^{12})_2$, $NO_2$, CN, $COOR^{12}$, $CON(R^{12})_2$, $NR^{12}COA$, $NR^{12}CON(R^{12})_2$, $NR^{12}SO_2 A$, $COR^{12}$, $SO_2 N(R^{12})_2$, $S(O)_n A$, $[C(R^{12})_2]_m COOR^{12}$ and/or $O[C(R^{12})_2]_m COOR^{12}$, |
| Het' | denotes a mono- or bicyclic saturated, unsaturated or aromatic heterocycle having 1 to 4 N, O and/or S atoms, which may be mono-, di- or trisubstituted by Hal, A, $OR^{12}$, $N(R^{12})_2$, $NO_2$, CN, $COOR^{12}$, $CON(R^{12})_2$, $NR^{12}COA$, $NR^{12}SO_2 A$, $COR^{12}$, $SO_2 N(R^{12})_2$, $S(O)_n A$, =S, =$NR^{12}$ and/or =O (carbonyl oxygen), |
| $R^{12}$ | denotes H or unbranched or branched alkyl having 1, 2, 3, 4, 5 or 6 C atoms or denotes cycloalkyl having 3-7 C atoms, unsubstituted or monosubstituted by =O, |
| Hal | denotes F, Cl, Br or I, |
| m | denotes 0, 1, 2, 3 or 4, |
| n | denotes 0, 1 or 2, | and pharmaceutically usable salts and stereoisomers thereof, including mixtures thereof in all ratios.

2. A compound according to claim 1, wherein
$R^1$, $R^3$, $R^5$ each denote H,
and pharmaceutically usable salts and stereoisomers thereof, including mixtures thereof in all ratios.

3. A compound according to claim 1, wherein
$R^2$, $R^4$ each denote, independently of one another, OA, Hal, $O[C(R^{12})_2]_m Het$ or $O[C(R^{12})_2]_m Ar$,
and pharmaceutically usable salts and stereoisomers thereof, including mixtures thereof in all ratios.

4. A compound according to claim 1, wherein
$R^6$, $R^7$ each, independently of one another, denote H or A,
and pharmaceutically usable salts and stereoisomers thereof, including mixtures thereof in all ratios.

5. A compound according to claim 1, wherein

A denotes unbranched or branched alkyl having 1-10 C atoms, in which one or two non-adjacent $CH_2$ groups may be replaced by O and/or in addition 1-7H atoms may be replaced by OH, F and/or Cl, and pharmaceutically usable salts and stereoisomers thereof, including mixtures thereof in all ratios.

6. A compound according to claim 1, wherein

Ar denotes phenyl which is unsubstituted or monosubstituted by $SO_nR^{12}$, and pharmaceutically usable salts and stereoisomers thereof, including mixtures thereof in all ratios.

7. A compound according to claim 1, wherein

Het denotes a monocyclic saturated, unsaturated or aromatic heterocycle having 1 to 4 N, O and/or S atoms, which may be monosubstituted by $[C(R^{12})_2]_mCON(R^{12})_2$, A or =O (carbonyl oxygen), and pharmaceutically usable salts and stereoisomers thereof, including mixtures thereof in all ratios.

8. A compound according to claim 1, wherein

Het denotes furyl, thienyl, pyrrolyl, imidazolyl, pyridyl, pyrimidinyl, pyrazolyl, thiazolyl, pyrrolidinyl, piperidinyl, morpholinyl, tetrahydropyranyl or piperazinyl, each of which is unsubstituted or monosubstituted by $[C(R^{12})_2]_mCON(R^{12})_2$, A or =O (carbonyl oxygen), and pharmaceutically usable salts and stereoisomers thereof, including mixtures thereof in all ratios.

9. A compound according to claim 1, wherein $R^{12}$ denotes H or unbranched or branched alkyl having 1, 2, 3, 4, 5 or 6 C atoms and pharmaceutically usable salts and stereoisomers thereof, including mixtures thereof in all ratios.

10. A compound according to claim 1, wherein

| | |
|---|---|
| $R^1, R^3, R^5$ | each denote H, |
| $R^2, R^4$ | each denote, independently of one another, OA, Hal, $[O[C(R^{12})_2]_m$Het or $O[C(R^{12})_2]_m$Ar, |
| $R^6, R^7$ | each denote, independently of one another, H or A, |
| D | denotes Ar or Het, |
| A | denotes unbranched or branched alkyl having 1-10 C atoms, in which one or two non-adjacent $CH_2$ groups may be replaced by O and/or in addition 1-7 H atoms may be replaced by OH, F and/or Cl, |
| Alk | denotes unbranched or branched alkylene having 1, 2, 3 or 4 C atoms, |
| Ar | denotes phenyl which is unsubstituted or monosubstituted by $SO_nR^{12}$, |
| Het | denotes a monocyclic saturated, unsaturated or aromatic heterocycle having 1 to 4 N, O and/or S atoms, which may be monosubstituted by $[C(R^{12})_2]_mCON(R^{12})_2$, A or =O (carbonyl oxygen), |
| $R^{12}$ | denotes H or unbranched or branched alkyl having 1, 2, 3, 4, 5 or 6 C atoms, |
| Hal | denotes F, Cl, Br or I, |
| m | denotes 0, 1, 2, 3 or 4, |
| n | denotes 0, 1 or 2, | and pharmaceutically usable salts and stereoisomers thereof, including mixtures thereof in all ratios.

11. A compound according to claim 1, wherein

| | |
|---|---|
| $R^1, R^3, R^5$ | each denote H, |
| $R^2, R^4$ | each denote, independently of one another, OA, Hal, $[O[C(R^{12})_2]_m$Het or $O[C(R^{12})_2]_m$Ar, |
| $R^6, R^7$ | each denote, independently of one another, H or A, |
| D | denotes Ar or Het, |
| A | denotes unbranched or branched alkyl having 1-10 C atoms, in which one or two non-adjacent $CH_2$ groups may be replaced by O and/or in addition 1-7 H atoms may be replaced by OH, F and/or Cl, |
| Alk | denotes unbranched or branched alkylene having 1, 2, 3 or 4 C atoms, |
| Ar | denotes phenyl which is unsubstituted or monosubstituted by $SO_nR^{12}$, |
| Het | denotes furyl, thienyl, pyrrolyl, imidazolyl, pyridyl, pyrimidinyl, pyrazolyl, thiazolyl, pyrrolidinyl, piperidinyl, morpholinyl, tetrahydropyranyl or piperazinyl, each of which is unsubstituted or monosubstituted by $[C(R^{12})_2]_mCON(R^{12})_2$, A or =O (carbonyl oxygen), |
| $R^{12}$ | denotes H or unbranched or branched alkyl having 1, 2, 3, 4, 5 or 6 C atoms, |
| Hal | denotes F, Cl, Br or I, |
| m | denotes 0, 1, 2, 3 or 4, |
| n | denotes 0, 1 or 2, | and pharmaceutically usable salts and stereoisomers thereof, including mixtures thereof in all ratios.

12. A compound according to claim 1, wherein $R^{12}$ denotes H or $CH_3$, and pharmaceutically usable salts and stereoisomers thereof, including mixtures thereof in all ratios.

13. A compound according to claim 1 selected from

| no. | name and/or structure |
|---|---|
| "A1" | 3-Benzyloxy-5-isopropoxy-N-(1-pyridine-2-ylmethyl-1H-pyrazol-3-yl)-benzamide |
| "A2" | 3-Benzyloxy-5-isopropoxy-N-(5-methyl-1-pyridine-2-ylmethyl-1H-pyrazole-3-yl)-benzamide |
| "A3" | 3-Benzyloxy-N-(1-benzyl-1H-pyrazol-3-yl)-5-isopropoxy-benzamide |
| "A4" | N-(1-Benzyl-1H-pyrazole-3-yl)-3-((S)-2-methoxy-1-methyl-ethoxy)-5-((S)-1-methyl-2-phenyl-ethoxy)-benzamide |
| "A5" | 3-((S)-2-Methoxy-1-methyl-ethoxy)-5-((S)-1-methyl-2-phenyl-ethoxy)-N-(1-pyridine-2-ylmethyl-1H-pyrazole-3-yl)-benzamide |
| "A6" | 3-Isopropoxy-N-(1-pyridine-2-ylmethyl-1H-pyrazole-3-yl)-5-(2-thiophene-3-yl-ethoxy)-benzamide |
| "A7" | 3-((S)-2-Methoxy-1-methyl-ethoxy)-5-((S)-1-methyl-2-phenyl-ethoxy)-N-(1-pyridine-3-ylmethyl-1H-pyrazole-3-yl)-benzamide |
| "A8" | 3-((S)-2-Methoxy-1-methyl-ethoxy)-5-((S)-1-methyl-2-phenyl-ethoxy)-N-(1-pyridine-4-ylmethyl-1H-pyrazole-3-yl)-benzamide |
| "A9" | N-(1-Benzyl-1H-pyrazol-3-yl)-3-isopropoxy-5-(2-thiophen-3-yl-ethoxy)-benzamide |
| "A10" | 3-(4-methanesulfonyl-phenoxy)-5-((S)-2-methoxy-1-methyl-ethoxy)-N-(1-pyridin-3-ylmethyl-1H-pyrazol-3-yl)-benzamide | and pharmaceutically usable salts and stereoisomers thereof, including mixtures thereof in all ratios.

14. A process for the preparation of compounds of the formula I according to claim 1 and pharmaceutically usable salts and stereoisomers thereof,
said process comprising:
reacting a compound of formula II

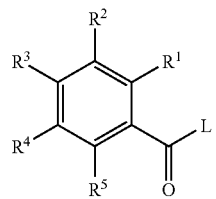

in which
L denotes Cl, Br, I or a free or reactively functionally modified OH group and
$R^1$, $R^2$, $R^3$, $R^4$ and $R^5$ have the meanings indicated in claim 1,
with a compound of formula III

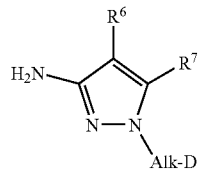

in which
Alk, D, $R^6$ and $R^7$ have the meanings indicated in claim 1,
and/or
converting a base or acid of the formula I into one of its salts.

15. A pharmaceutical composition comprising at least one compound according to claim 1 and at least one excipient and/or adjuvant.

16. A method for the treatment of a disease or condition resulting from underactivity of glucokinase or which can be treated by activating glucokinase, comprising administering to a patient an effective amount of a compound according to claim 1.

17. A method according to claim 16, where the disease or condition is insulin-dependent diabetes mellitus, non-insulin-dependent diabetes mellitus, obesity, neuropathy and/or nephropathy.

18. A pharmaceutical composition comprising at least one compound according to claim 1 and at least one further medicament active ingredient.

19. A kit comprising separate packs of
(a) an effective amount of a compound according to claim 1, and
(b) an effective amount of a further medicament active ingredient.

20. A compound according to claim 3, wherein $R^{12}$ is H.

21. A compound according to claim 4, wherein $R^6$ and $R^7$ are each, independently of one another, H or methyl, ethyl, propyl, isopropyl or butyl.

22. A compound according to claim 1, wherein $R^{10}$ and $R^{11}$ are each H.

* * * * *